United States Patent
McFarland et al.

(10) Patent No.: US 11,995,558 B2
(45) Date of Patent: May 28, 2024

(54) APPARATUS FOR HIGH DENSITY INFORMATION STORAGE IN MOLECULAR CHAINS

(71) Applicant: The Charles Stark Draper Laboratory, Inc., Cambridge, MA (US)

(72) Inventors: Kirsty A. McFarland, Melrose, MA (US); Andrew P. Magyar, Arlington, MA (US); Ian Ward Frank, Arlington, MA (US); Kenneth T. Kotz, Newton, MA (US); Stacey Markovic, Boston, MA (US); Haiyao Huang, Cambridge, MA (US); Steven J. Byrnes, Watertown, MA (US); Gregg E. Favalora, Bedford, MA (US); Melissa M. Sprachman, Somerville, MA (US); Ryan A. Dubay, Ludlow, MA (US); Emma Vargo, Berkeley, CA (US); Peter Cavanagh, Stanford, CA (US); Erin Rosenberger, Quincy, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 711 days.

(21) Appl. No.: 16/415,666

(22) Filed: May 17, 2019

(65) Prior Publication Data
US 2019/0354871 A1    Nov. 21, 2019

Related U.S. Application Data

(60) Provisional application No. 62/672,972, filed on May 17, 2018.

(51) Int. Cl.
| | |
|---|---|
| *G06N 3/12* | (2023.01) |
| *B01L 3/00* | (2006.01) |
| *B81B 1/00* | (2006.01) |
| *C12N 9/12* | (2006.01) |
| *C12N 15/10* | (2006.01) |
| *C12P 19/34* | (2006.01) |
| *G06N 3/123* | (2023.01) |
| *G11C 13/02* | (2006.01) |

(52) U.S. Cl.
CPC ............ *G06N 3/123* (2013.01); *B01L 3/5027* (2013.01); *B01L 3/502761* (2013.01); *B01L 3/50851* (2013.01); *B01L 3/527* (2013.01); *B81B 1/006* (2013.01); *C12N 9/12* (2013.01); *C12N 15/1006* (2013.01); *C12N 15/1065* (2013.01); *C12N 15/1068* (2013.01); *C12P 19/34* (2013.01); *G11C 13/02* (2013.01); *B01J 2219/00495* (2013.01)

(58) Field of Classification Search
CPC .......... B01L 3/502761; B01L 3/50851; B01L 3/527; C12N 15/1006; C12P 19/34
See application file for complete search history.

(56) References Cited

U.S. PATENT DOCUMENTS

| | | | |
|---|---|---|---|
| 5,243,540 A | 9/1993 | Van Albert et al. | |
| 5,840,841 A * | 11/1998 | Zuckermann | C07K 1/047 |
| | | | 530/338 |
| 6,232,066 B1 | 5/2001 | Felder et al. | |
| 6,238,869 B1 | 5/2001 | Kris et al. | |
| 6,664,079 B2 | 12/2003 | Ju et al. | |
| 6,819,469 B1 * | 11/2004 | Koba | G03H 1/02 |
| | | | 359/290 |
| 7,883,869 B2 | 2/2011 | Ju et al. | |
| 9,384,320 B2 | 7/2016 | Church | |
| 9,708,358 B2 | 7/2017 | Ju et al. | |
| 9,833,761 B2 * | 12/2017 | Banyai | C12N 15/74 |
| 9,897,791 B2 | 2/2018 | Feng | |
| 9,928,869 B2 | 3/2018 | Church | |
| 9,996,778 B2 | 6/2018 | Church | |
| 10,605,734 B2 | 3/2020 | Lafferty et al. | |
| 2002/0001075 A1 | 1/2002 | Tsien et al. | |
| 2002/0081582 A1 | 6/2002 | Gao et al. | |
| 2003/0143132 A1 | 7/2003 | Cerrina et al. | |
| 2004/0071394 A1 | 4/2004 | Gfrorer et al. | |
| 2004/0197793 A1 | 10/2004 | Hassibi et al. | |
| 2006/0154264 A1 | 7/2006 | Cerrina | |
| 2007/0116607 A1 | 5/2007 | Wang et al. | |
| 2007/0224616 A1 * | 9/2007 | Gulari | B01J 19/0046 |
| | | | 435/6.12 |
| 2008/0085564 A1 | 4/2008 | Hartzell et al. | |
| 2009/0023609 A1 | 1/2009 | Jung et al. | |
| 2011/0092380 A1 | 4/2011 | Stahler et al. | |
| 2015/0269313 A1 | 9/2015 | Church | |
| 2016/0358055 A1 * | 12/2016 | Church | G06N 3/123 |
| 2019/0009240 A1 | 1/2019 | Magyar et al. | |
| 2019/0112626 A1 | 4/2019 | Lee et al. | |
| 2019/0112627 A1 | 4/2019 | Arlow et al. | |

FOREIGN PATENT DOCUMENTS

| | | | |
|---|---|---|---|
| EP | 0969083 | 5/2000 | |
| EP | 1215623 | 6/2002 | |
| WO | WO 2008049795 | 5/2008 | |
| WO | WO-2012154201 A1 * | 11/2012 | ......... C12N 15/1031 |
| WO | WO 2017156218 | 9/2017 | |
| WO | WO-2017156218 A1 * | 9/2017 | ............. C12P 19/34 |
| WO | WO 2017189794 | 11/2017 | |
| WO | WO 2017222710 | 12/2017 | |
| WO | WO 2017223517 | 12/2017 | |
| WO | WO 2018102554 | 6/2018 | |

(Continued)

OTHER PUBLICATIONS

Blair et al. ("A scalable method for multiplex LED-controlled synthesis of DNA in capillaries." Nucleic Acids Research 34.16 (2006): e110; 8 pages) (Year: 2006).*

(Continued)

*Primary Examiner* — Sahana S Kaup
(74) *Attorney, Agent, or Firm* — HoustonHogle LLP

(57) ABSTRACT

A parallelized chain-synthesizing technique includes capillary tubes, where each tube provides multiple locations or addresses where a specific arbitrary sequence for polymeric chains can be synthesized. An optical addressing system selectively delivers light to the locations to mediate or control reactions in the tubes.

24 Claims, 16 Drawing Sheets

(56) References Cited

FOREIGN PATENT DOCUMENTS

| WO | WO 2018119253 | 6/2018 |
| WO | WO 2019079802 | 10/2018 |
| WO | WO 2018217689 | 11/2018 |

OTHER PUBLICATIONS

Zhirnov et al. ("Nucleic acid memory." Nature materials 15.4 (2016): 366-370). (Year: 2016).*

Yuen ("A reconfigurable stick-n-play modular microfluidic system using magnetic interconnects." Lab on a Chip 16.19 (2016): 3700-3707.). (Year: 2016).*

International Preliminary Report on Patentability, dated Dec. 5, 2019, from International Application No. PCT/US2018/033798, filed on May 22, 2018. 9 pages.

Hoppmann, C. et al., "Photoswitchable Click Amino Acids: Light Control of Conformation and Bioactivity," ChemBioChem, 12(17):2555-2559 (2011).

International Search Report and Written Opinion of the International Searching Authority, dated Sep. 21, 2018, from International Application No. PCT/US2018/033798, filed on May 22, 2018. 18 pages.

König, N.F., et al., "Photocontrolled Synthesis of Abiotic Sequence-Defined Oligo (Phosphodiester)s," Macromolecular rapid communications, 38(24):1700651 (2017).

Marcandalli, B. et al., "Thermodynamic Study of Solvent and Substituent Effects on 4-Substituted Aminoazobenzenes," Dyes and Pigments, 8(4):239-251 (1987).

Tuuttila, T. et al., "Chiral donor-pi-acceptor azobenzene dyes," Dyes and Pigments, 80(1):34-40 (2009).

XP-002784474, Mouse terminal deoxynucleotidyl transferase (TdT), SEQ ID 9. Retrieved from EBI accession No. GSP:BCP96833 (2016).

Zhang, J. et al., "Synthesis and confirmational study of novel, stable, helical poly(N-propargylamides) containing dipole azobenzene chromophores in the side chains," Polym. Bull., 71(11):2803-2818 (2014).

Partial Search Report of the International Searching Authority, dated Sep. 2, 2019, from International Application No. PCT/US2019/032903, filed on May 17, 2019. 10 pages.

Boukhet, M., et al., "Translocation of Precision Polymers through Biological Nanopores," Macromol. Rapid Commun. 38 (24), 1700680: 1-6 (2017).

International Search Report and Written Opinion, dated Oct. 26, 2018, from International Application No. PCT/US2018/041397, filed on Jul. 10, 2018. 19 pages.

Ju, J., et al., "Four-color DNA sequencing by synthesis using cleavable fluorescent nucleotide reversible terminators," Proceedings of the National Academy of Sciences, 103(52): 19635-19640 (2006).

Klein, J.C., et al., "Multiplex pairwise assembly of array-derived DNA oligonucleotides," Nucleic Acids Research, 44(5): 1-10, e43 (2016).

Orski, S.V., et al., "High density orthogonal surface immobilization via photoactivated copper-free click chemistry," J.Am. Chem. Soc., 132 (32), 11024-11026 (2010).

Palluk, S., et al., "De novo DNA Synthesis Using Polymerase Nucleotide Conjugates," Nature Biotechnology, 36(7): 645-650 (2017).

Partial Search Report of the International Searching Authority, dated Sep. 3, 2018, from International Application No. PCT/US2018/041397, filed on Jul. 10, 2018. 12 pages.

Samanta, S., et al., "Bidirectional Photocontrol of Peptide Conformation with a Bridged Azobenzene Derivative," Angew. Chem. Int. Ed., 51: 6452-6455 (2012).

International Preliminary Report on Patentability, dated Nov. 26, 2020, from International Application No. PCT/US2019/032903, filed on May 17, 2019. 10 pages.

International Preliminary Report on Patentability dated Jan. 23, 2020, from International Application No. PCT/US2018/041397, filed on Jul. 10, 2018. 12 pages.

International Search Report and Written Opinion of the International Searching Authority, dated Oct. 25, 2019, from International Application No. PCT/US2019/032903, filed on May 17, 2019. 18 pages.

Amiram, M., et al., "Evolution of Translation Machinery in Recoded Bacteria Enables Multi-Site in Incorporation of Nonstandard Amino Acids," Nature Biotechnology, 33(12): 1272-1282 (2015).

Chi, L., et al., "A Blue-Green Absorbing Cross-Linker for Rapid Photoswitching of Peptide Helix Content," Bioconjugate Chem., 17: 670-676 (2006).

Clardy, S.M., et al., "Fluorescent Exendin-4 Derivatives for Pancreatic β-Cell Analysis," Bioconjugate Chem., 25: 171-177 (2014).

Costi, R., et al., "New Nucleotide-Competitive Non-Nucleoside Inhibitors of Terminal Deoxynucleotidyl Transferase: Discovery, Characterization, and Crystal Structure in Complex with the Target," J. Med. Chem., 56: 7431-7441 (2013).

Delarue, M., et al., "Crystal Structure of a Template-Independent DNA Polymerase: Murine Terminal Deoxynucleotidyltransferase," EMBO Journal, 21(3): 427-439 (2002).

Gouge, J., et al., "Structure of Intermediates Along the Catalytic Cycle of Terminal Deoxynucleotidyltransferase: Dynamical Aspects of the Two-Metal Ion Mechanism," J. Mol. Biol., 425: 4334-4352 (2013).

Hamon, F., et al., "Azobenzenes—Synthesis and Carbohydrate Applications," Tetrahedron, 65: 10105-10123 (2009).

Jewett, J.C., et al., "Rapid Cu-Free Click Chemistry with Readily Synthesized Biarylazacyclooctynones," J. Am. Chem. Soc., 132: 3688-3690 (2010).

Karver, M.R., et al., "Bioorthogonal Reaction Pairs Enable Simultaneous, Selective, Multi-Target Imaging," Angew. Chem. Int. Ed., 51: 920-922 (2012).

Kienzler, M.A., et al., "A Red-Shifting, Fast-Relaxing Azobenzene Photoswitch for Visible Light Control of an Ionotropic Glutamate Receptor," J. Am., Chem. Soc., 135: 17683-17686 (2013).

Kolb, H.C., et al., "Click Chemistry: Diverse Chemical Function from a Few Good Reactions," Angew. Chem. Int. Ed., 40: 2004-2021 (2001).

Konig, N.F., et al., "Photocontrolled Synthesis of Abiotic Sequence-Defined Oligo(Phosphodiester)s," Macromol. Rapid Commun., 38: 1700651 (2017).

Li, L., et al., "A Switchable Two-Photon Membrane Tracer Capable of Imaging Membrane-Associated Protein Tyrosine Phosphatase Activities," Angew. Chem. Int. Ed., 52: 424-428 (2013).

Loh, Y., et al., ""Click" Synthesis of Small Molecule-Peptide Conjugates for Organelle-Specific Delivery and Inhibition of Lysosomal Cysteine Protease," Chem. Commun., 46: 8407-8409 (2010).

Moon, A.F., et al., "Structural Insight into the Substrate Specificity of DNA Polymerase μ," Nature Structural & Molecular Biology, 14(1): 45-54 (2007).

Patterson, D.M., et al., "Finding the Right (Bioorthogonal) Chemistry," ACS Chem. Biol., 9: 592-605 (2014).

Pickens, C.J., et al., "Practical Considerations, Challenges, and Limitations of Bioconjugation via Azide-Alkyne Cycloaddition," Bioconjugate Chem., 29: 686-701 (2018).

Rashidian, M., et al., "Use of 18F-2-Fluorodeoxyglucose to Label Antibody Fragments for Immuno-Positron Emission Tomography of Pancreatic Cancer," ACS Cent. Sci., 1: 142-147 (2015).

Reis, S.A., et al.,"Light-Controlled Modulation of Gene Expression by Chemical Optoepigentic Probes," Nature Chemical Biology, 12: 317-326 (2016).

White, E.R., et al., "Replacing Amino Acids in Translation: Expanding Chemical Diversity with Non-Natural Variants," Methods, 60: 70-74 (2013).

Zeglis, B.M., et al., "Building Blocks for the Construction of Bioorthogonally Reactive Peptides via Solid-Phase Peptide Synthesis," ChemistryOpen, 3: 48-53 (2014).

Kumar, K.R.S., et al., "Complete On/Off Photoswitching of the Motility of a Nanobiomolecular Machine," ACS Nano, 8(5): 4157-4165 (2014).

(56) References Cited

OTHER PUBLICATIONS

Mousavi, S.A., et al., "Glutamate Receptor-Like Genes Mediate Leaf-to-Leaf Signaling," Nature, 500(7463): 422-426 (2013).

Modak, M.J., et al., "Biochemistry of Terminal Deoxynucleotidyl Transferase," The Journal of Biochemistry, 257(24): 15105-15109 (1982).

Motea, E.A., et al., "Terminal Deoxynucleotidyl Transferase: The Story of a Misguided DNA Polymerase," Bfochimica et Biophysica Acta, 1804, 1151-1166 (2010).

Poloni, C., et al., "A Fast, Visible-Light-Senstitive Azobenzene for Bioorthogonal Ligation," Chern. Eur. J., 20, 946-951 (2014).

Magnus, P., et al., "Direct N-Alkyl Azidonation of N,N-Dialkylarylamines with the Iodosylbenzene/Trimethylsilylazide Reagent Combination," J. Am. Chern. Soc, 115: 9347-9348 (1993).

Maezawa et al., "Ubiquitylation of Terminal Deoxynucle-otidyltransferase Inhibits Its Activity" PLoS One (2012), 7(7), e39511, 15 pages. (Year: 2012).

Blackman et al., "Tetrazine Ligation: Fast Bioconjugation Based on Inverse-Electron-Demand Diels-Alder Reactivity" JACS (2008), 130(41), 13518-13519. (Year: 2008).

\* cited by examiner

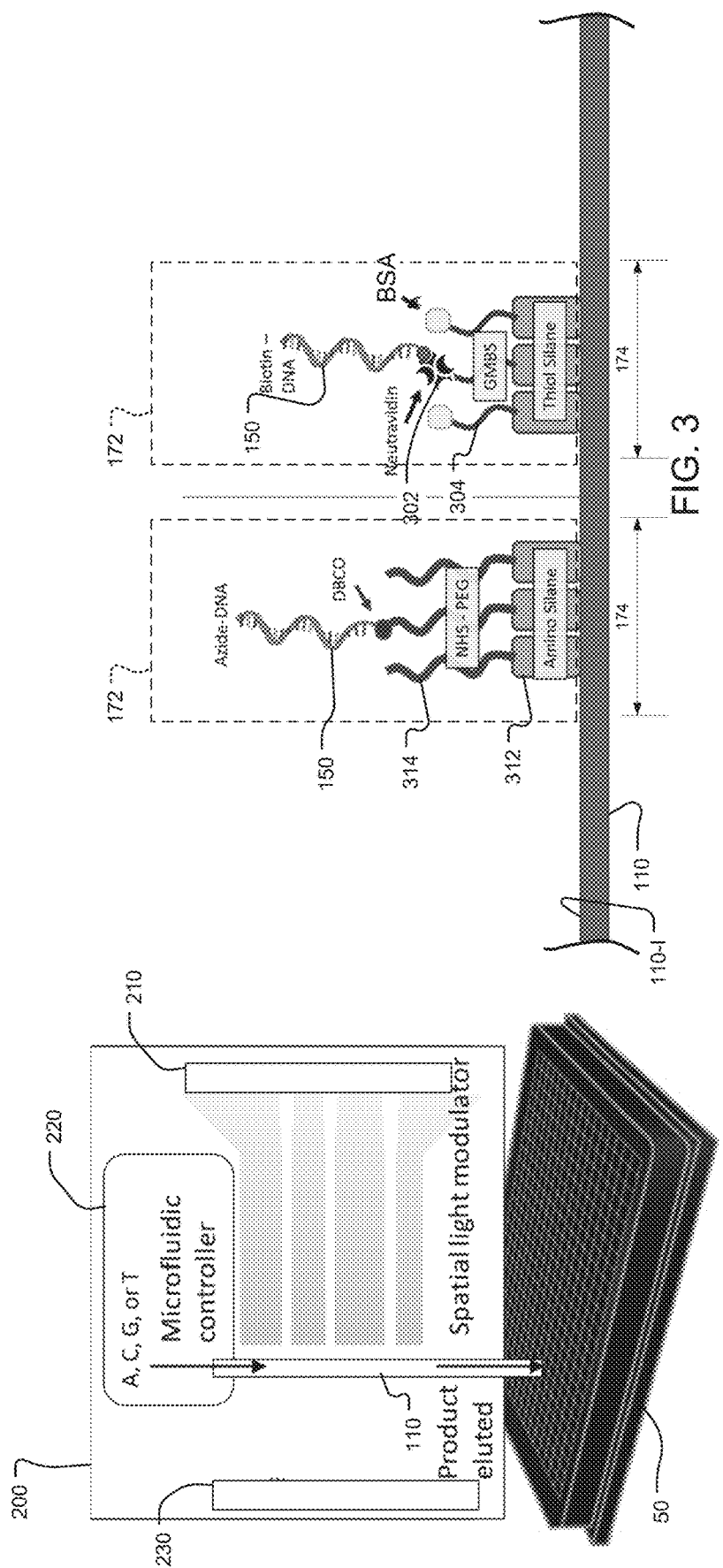

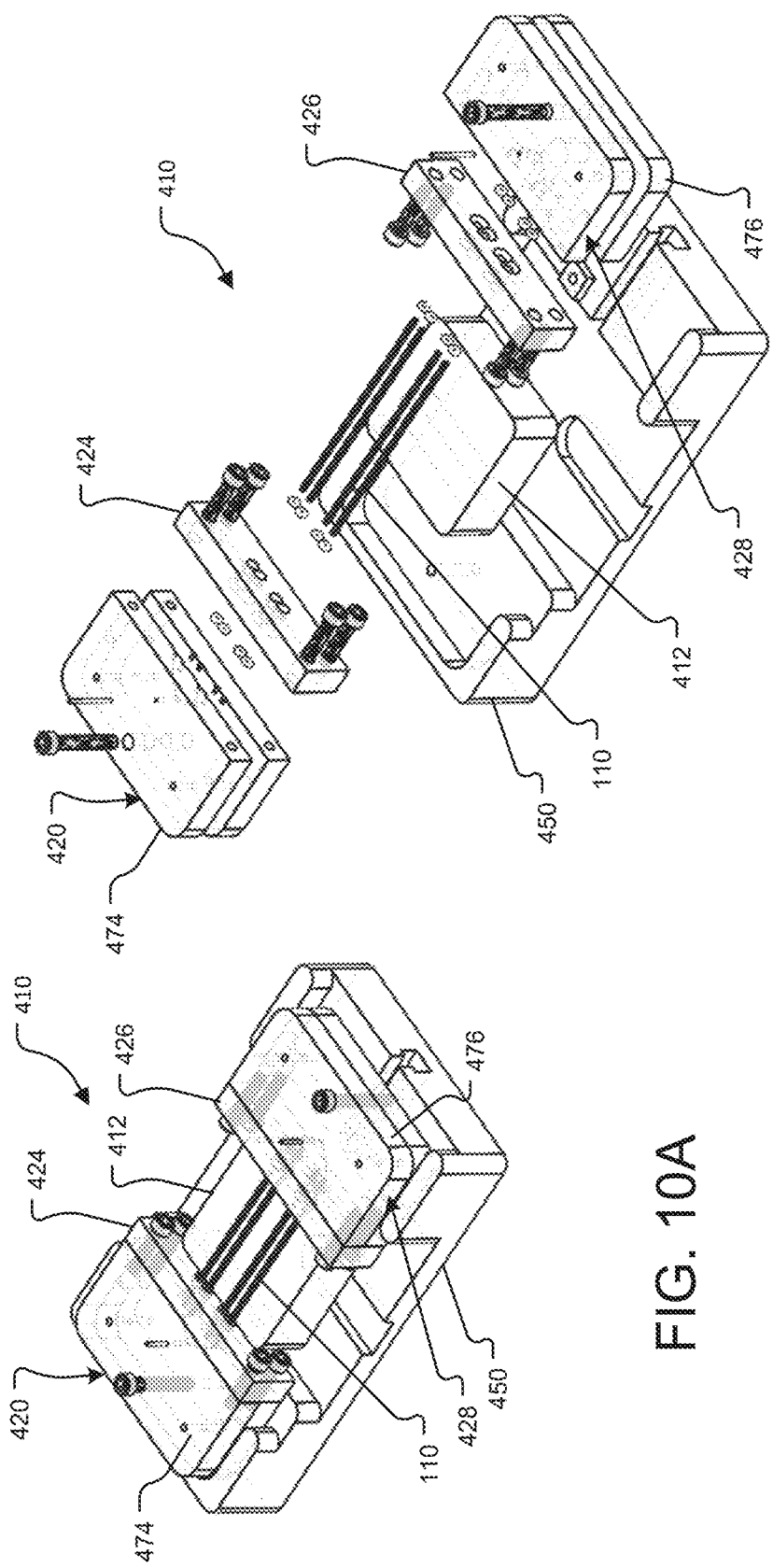

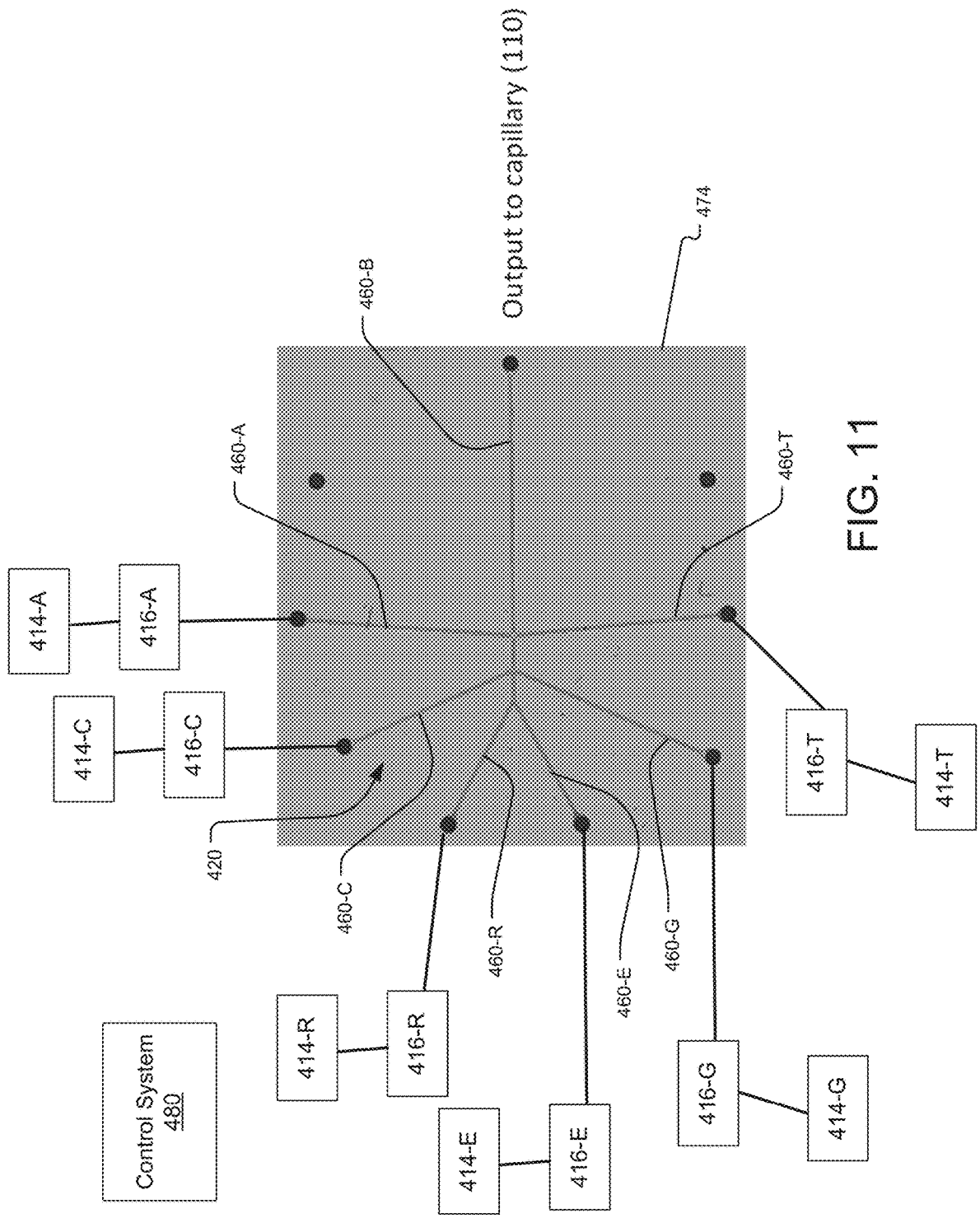

APPARATUS FOR HIGH DENSITY INFORMATION STORAGE IN MOLECULAR CHAINS

RELATED APPLICATIONS

This application claims the benefit under 35 USC 119(e) of U.S. Provisional Application No. 62/672,972, filed on May 17, 2018, which is incorporated herein by reference in its entirety.

BACKGROUND OF THE INVENTION

International Patent Application No. PCT/US18/33798, filed on May 22, 2018, by Magyar, et al., (International Publication No. WO 2018/217689) which is incorporated herein by this reference in its entirety (hereinafter Magyar I), concerns the control of DNA synthesis. Specifically, it concerns Terminal Deoxynucleotidyl Transferase (TDT or TdT) engineering, which is the control of the catalytic cycle of TDT for DNA synthesis technology. TDT is an enzyme that is capable of catalyzing the addition of nucleotide triphosphates and analogs to the 3' ends of strands of DNA.

The Magyar I describes the catalytic cycle of TDT. The enzyme has two major activities during in vitro non-template DNA synthesis. These activities are transferring nucleotides onto the three-prime end of a growing DNA strand, and ratcheting down the strand of DNA in order to position the active site such that the next nucleotide can be added. A number of methodologies are presented for controlling the catalytic cycle for single nucleotide insertion. The enzyme can be further engineered such that only a single base can be controllably inserted at a time. Some approaches described involve control of DNA synthesis by modulating the temperature, pH, light or other aspects of the environment.

The ability to control the synthesis of DNA or other polymeric chains has great promise for ultrahigh density storage of information as described in International Patent Application No. PCT/US18/41397, filed on Jul. 10, 2018, by Magyar, et al., (International Publication No. WO 2019/014185) which is incorporated herein by this reference in its entirety (hereinafter Magyar II). Here, the chains are synthesized in wells that are optically addressed. The described apparatus enables large arrays of chains to be contained and synthesized in a compact and scalable manner. Each well provides a location where a specific arbitrary sequence can be synthesized. A piece of single-stranded DNA (SS-DNA) seeds the synthesis of the payload information in the DNA in each well. This addressing SS-DNA piece can be deposited a priori or synthesized as part of enzymatic process. The seed DNA acts as a primer for PCR (polymerase chain reaction) amplification and DNA sequencing.

Providing the necessary chemistry to each of the different wells is accomplished by dip coating or by means of microfluidics. The use of spatially and temporally gating an optical signal that is arbitrarily addressable to each well allows for the same sequence of raw materials to be delivered to every well simultaneously, with the optical gating determining the portion of the sequence delivered to the well that is incorporated into the chain or chains anchored in the specific well. A rinsing buffer can be delivered through the same channels that deliver the raw materials.

SUMMARY OF THE INVENTION

The present invention, in part, could be characterized as an extension of the approach described in Magyar II. Rather than wells, however, the polymeric chains, i.e., DNA strands, are synthesized in tube(s). Exemplary tubes include capillary tubes. The tubes can have different cross-sections such as circular, square or hexagonal, for example.

The invention further extends to the hardware and methods for synthesis of the polymeric chains such as DNA strands, as well as the means for storage, retrieval, and sequencing of the chains (DNA strands). Microfluidic pumping systems can then be used to cycle the reagents required for DNA synthesis. Optical activation or deactivation of the DNA synthesis reaction enables spatially-controlled, multiplexed synthesis of a few to many strands, possibly $10^7$ DNA strands, per tube. Random access retrieval of individual DNA strands is enabled through the inclusion of DNA indices at one or both of the 3' and 5' end of each sequence that can be used for targeted PCR amplification or in situ sequencing. The DNA can be directly sequenced in the tube, such as with fluorescence-based sequencing, or the DNA can be eluted from the tubes and sequenced using commercial sequencers.

Embodiments described herein are believed to address challenges presented by the rapid increase in information, an increase that appears to outpace traditional storage devices. With information being stored at the molecular level, practicing aspects of the invention can result in highly dense storage of huge amounts of information. It is estimated, for example, (Robert F. Service, Science, Mar. 2, 2017, 2:00 PM) that DNA could store all of the world's data in one room. Furthermore, polymeric chains such as DNA, if stored properly, can have exceptional longevity. DNA from the era of the dinosaurs has been decoded. Thus, unlike conventional storage media, DNA would not become obsolete or corrupted. Moreover, data stored in this form can be copied, and edited.

In general, according to one aspect, the invention features a polymeric chain-synthesizing method. This method comprises immobilizing seed molecules in a tube and selectively delivering light to different locations of the tube to mediate or control chemical reactions for synthesis of sequences from the seed molecules to thereby synthesize polymeric chains.

Often, the polymeric chains include DNA.

A number of techniques can be used to immobilize the seed molecules. Some examples are click chemistry, biotin-streptavidin interactions, or photo-cleavable or enzymatically-cleavable groups. The synthesis might then occur on a complementary DNA strand that is hybridized to the surface immobilized DNA molecule and leaves a 3' overhang.

The method will typically further involve the introduction of different reagents required for synthesis of the polymeric chains into the tube. For example, adenine (A), cytosine (C), guanine (G), thymine (T) could be introduced for the synthesis of DNA polymeric chains.

Microfluidics are helpful for controlled introductions of the reagents required for synthesis into the tube.

It can be desirable to store the polymeric chains in the tube. The polymeric chains could further be sequenced in the tube. In other cases, however, the polymeric chains might be eluted from the tube and then sequenced. The elution can be performed by heating the tube to dehybridize the synthesized chains.

Different seed molecules could be immobilized inside the tube to enable random access of the different chains.

The method can further include robotically retrieving the tube from a store to access information encoded in the polymeric chains in the tube. In situ sequencing of the chains using sequencing by synthesis, through the sequential microfluidic introduction of fluorescently labeled nucleotides and DNA polymerase and detection of fluorescence is also a possibility.

In general, according to another aspect, the invention features a method involving random access read/write of information to/from DNA in a tube wherein digital data is encoded in DNA through synthesis and decoded from DNA through sequencing.

In general, according to another aspect, the invention features a microfluidic manifold to hold capillary tubes enabling reagent delivery for DNA synthesis. Conveniently, a magnet could be used to secure and fluidically seal an interface to the capillary tube.

In general, according to another aspect, the invention features a parallelized chain-synthesizing apparatus. This apparatus comprises at least one tube, in which different arbitrary sequences of polymeric chains are synthesized and an optical addressing system for selective delivery of light to different locations on the tube to mediate or control chemical reactions for the synthesis of the different sequences at the locations.

In embodiments, the tube might be a capillary tube. Further, the locations might be distributed along a longitudinal length of the tube and/or at different circumferential positions along an inner surface of the tube.

In general, according to a different aspect, the invention features a parallelized chain-synthesizing apparatus, comprising volumetric regions in which different arbitrary sequences of polymeric chains are synthesized and a spatial light modulator that selectively delivers light to different volumetric regions to mediate or control chemical reactions for the synthesis of the different sequences at the regions.

The spatial light modulator might be a micromirror device or a liquid crystal on silicon device.

The spatial light modulator might project a hologram into the volumetric regions.

In embodiments, the volumetric regions are in a tube.

In general, according to another aspect, the invention features a tube with immobilized seed molecules inside.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 2 is a schematic diagram illustrating the approach for retrieval of individual or groups of DNA strands from a tube typically for sequencing outside the tube.

FIG. 3 is a schematic partial side cross-sectional view showing a portion of a capillary tube with immobilized DNA strands and the volumetric region within the tube in which the strands are synthesized.

FIGS. 5B and 5C are based on "Bidirectional Photocontrol of Peptide Conformation with a Bridged Azobenzene Derivative", Angew. Chem. Int. Ed. 51, 6452-6455 (2012).

FIG. 10A is a perspective view and FIG. 10B is an exploded perspective view of an example of the manifold system.

FIG. 11 is a schematic diagram showing a microfluidic input manifold fabricated from silicon and its internal channels for supplying fluid to a capillary tube.

DETAILED DESCRIPTION OF THE PREFERRED EMBODIMENTS

Figure 1:
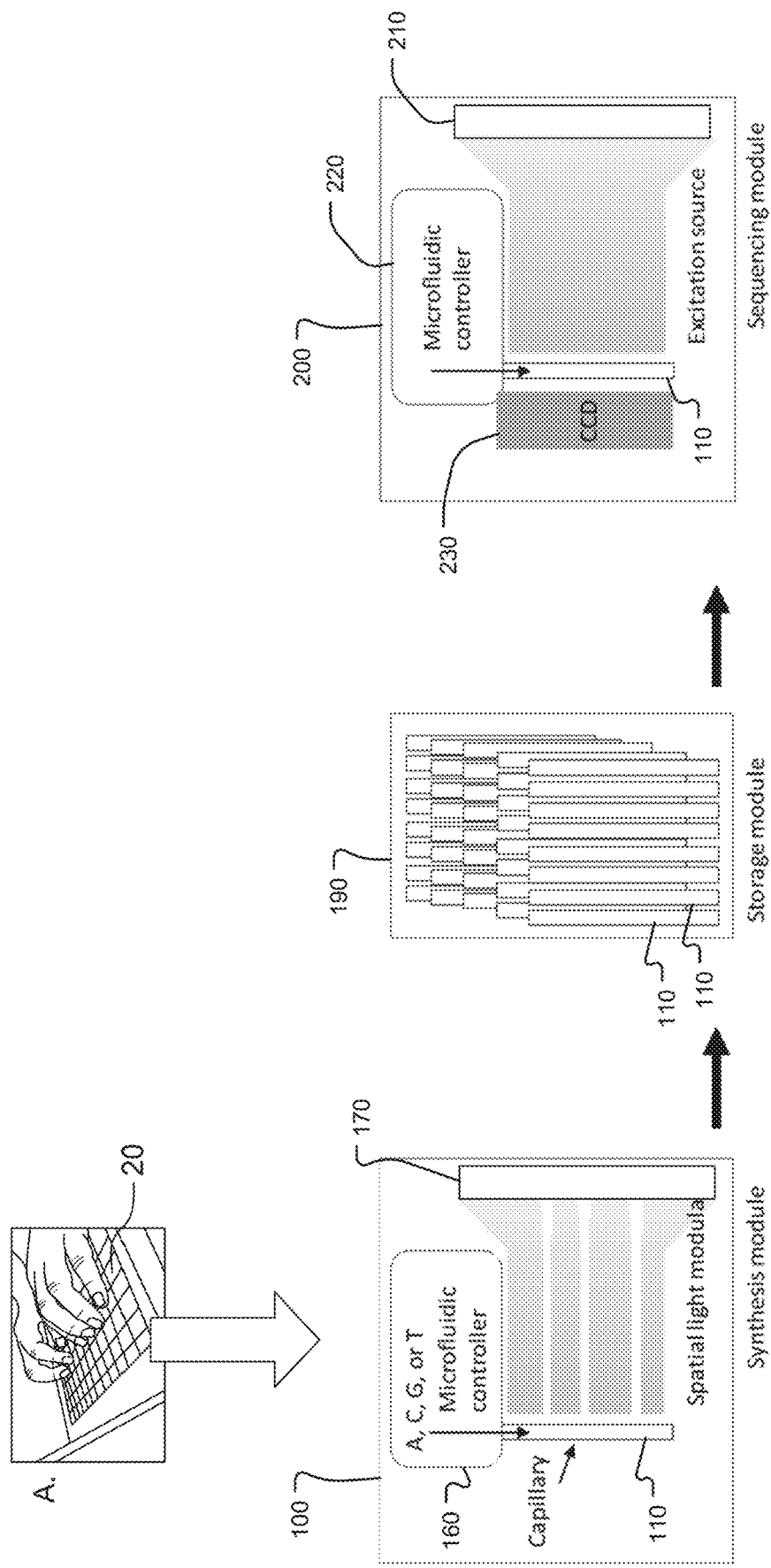
FIG. 1 is a schematic diagram illustrating the approach for using the parallelized chain-synthesizing apparatus for data encoding and storage using polymeric chains in capillary tubes.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

A common technique in combinatorial chemistry, "parallel synthesis" generally refers to the preparation of chemical structure combinations by separate and parallel syntheses, using multiple, often thousands of reaction vessels. Typically, the method employs robotics programmed to add the appropriate reagents to each vessel and generates libraries based on a specific skeleton (starting compound).

In this type of combinatorial approach, compounds are synthesized in parallel and in spatially separated compartments, using a "one vessel-one compound" principle. The reactions can be conducted on a solid support or in a liquid phase (solution chemistry). In many implementations, the vessel is a 96 well microtiter plate (MTP), or another suitable array.

The present systems and methods extend this combinatorial approach to tube-based reaction vessels. In these vessels, different addresses correspond to different locations within the tubes such as different locations such as around the inner walls of the tubes or otherwise within the volumetric regions contained in the tubes. Each location corresponds to a unique address and different pieces of single-stranded DNA, or other sequence-controlled polymeric chains, immobilized at these locations function as primers for synthesis, or seed molecules, on which the payload information is encoded as a DNA sequence. In addition to the encoded data, the immobilized seed DNA molecules contain a known sequence that is used for PCR amplification and DNA sequencing. At each unique location, the same DNA sequence is created. Reactions in the tubes are preferably mediated, gated or controlled at least partially using radiation, such as optically. This single strand could be deposited as part of the preparation for the synthesis or created de novo during synthesis.

A major application of this technology relates to data encoding and storing. Examples of data that can be encoded include but are not limited to electronic files, databases, manuscripts, graphics, computer programs, experimental data, spreadsheets, libraries, genetic information, and so forth, in encrypted, compressed, or un-modified form.

FIG. 1 is an illustrative diagram showing how parallelized chain-synthesis techniques can be used in data encoding and storage processes. In the download phase, data, e.g., a file, initially stored on a computer 20, such as a personal computer, or another suitable device, is downloaded to a parallelized chain synthesizer 100. The parallelized chain synthesizer is designed to construct, simultaneously, multiple chains that encode the information from the input data (e.g., file). Typically, different chains encode different portions of the file.

The next stage is the writing, which involves encoding the file as a collection of relatively short (100 to 1000 to 10000, or more base pairs, for example) DNA/oligo strands that can be in an aqueous solution or another suitable medium. Encryption and error correction can be applied to transform the file prior to synthesis.

The optimal length of the encoded strands is determined by the write error rate, the read error rate, and spatial constraints due to the finite well size and lengths of SS-DNA.

In the illustrated example, the strands are created in a tube 110. The tube or capillary tube is defined as a thin (10-2000 micrometer) linear or curved enclosed channel embedded in a substrate, which is typically hard such as glass. The channel may have a circular, square, or rectangular or other cross-sections. Channels can also be arrayed in a parallel manner in single monolithic substrate, described herein as a capillary array. Capillary tubes and arrays with a variety of geometries are commercially available from companies such as Vitrocom. The tube will also be transparent to the radiation (usually light) that is used to mediate the reactions and/or interrogate reactions involving the chains.

One particular key aspect relates to the tube's capacity for rapid fluid switching. This is important for being able to synthesize quickly. Preferably, the aspect ratio of the tube cross section is close to 1:1, as between 1:1 and 1:2. This is why a capillary tube, or a capillary tube array is a desirable geometry, rather than a single wide rectangular fluidic channel, for example. The capillary tube array enables maximal use of the active area of commercial SLMs or microdisplays, while maintaining rapid fluidic switching, and minimizing reagent consumption.

A microfluidic controller 160 provides different monomers to form the polymeric chains. In the case of a DNA strand, the different DNA bases (monomers), adenine (A), cytosine (C), guanine (G), thymine (T) and reagents are flowed through the tube 110, such as in a repeating sequence. At the same time, an optical controller 170, such as a spatial light modulator selectively illuminates the different locations in the channels to thereby mediate reactions involving the bases with the growing polymeric chains immobilized at those locations. Optical activation or deactivation of the DNA synthesis reaction enables spatially-controlled, multiplexed synthesis of up to $10^7$ DNA strands per tube using a single optical controller.

The collection of DNA/oligo strands can be stored and/or transported, e.g., in respective tubes 110 within a storage module 190, and possibly transported to a suitable destination. Then at a readout phase, sequencer (e.g., DNA sequencer 200) sequences or reads-out the data encoded in the strands. The sequencer 200 can be a commercial off the shelf (COTS) apparatus, a next generation DNA sequencer, or any suitable mechanism for reading DNA sequences.

The sequencer 200 will often similarly have an excitation source 210 for optically interrogating the DNA strands located at each of the locations within the tube 100. A sequencer microfluidic controller 220 flows the various fluids required for sequencing through the tube 110. An optical detector 230, such as a spatially resolved CCD or CMOS image sensor, detects the presence/absence of optical signals from each of the locations within the tube 110 due to the light from the excitation source.

FIG. 2 illustrates the potential for access retrieval of individual DNA sequences from a tube.

Strand retrieval is enabled through the inclusion of DNA indices at one or both of the 3' and 5' end of each sequence within the tube. This can be used for targeted PCR amplification or in situ sequencing using the excitation source 210 for access to the DNA strands located at each of the locations within the tube 100, the sequencer microfluidic controller 220 that flows the various fluids required for sequencing through the tube 110 or flushing selected sequences from the tube, and the optical detector 230, such as a spatially resolved CCD or CMOS image sensor that detects the presence of optical signals from each of the locations within the tube 110. The DNA can be eluted from the tube into a well of a microtiter plate 50 or any other appropriate vessel and then sequenced using commercial sequencers.

Preparation of Capillary Tube for Synthesis

FIG. 3 shows a portion of a capillary tube 110. To prepare a capillary tube for DNA synthesis, seed DNA molecules 150, which will serve as seeds for controlled DNA synthesis, are immobilized on the inside wall 110-1 of the capillary tube 110. The DNA seed 150 can be chemically attached to the surface by a variety of approaches, including through click chemistry or biotin streptavidin interactions. The downstream requirements for elution DNA recovery informs the selection of DNA immobilization chemistry. For example, the biotin-streptavidin interaction can be denatured enabling DNA strand elution from the surface 110-I using temperature or denaturing solutions. Alternatively, a photo-cleavable or enzymatically-cleavable group can be included into the seed DNA molecule 150 allowing it to be cleaved from the inside of the tube.

For one embodiment, biotin streptavidin interactions are used to attach the seed DNA molecule 150. First, the inside wall 110-I of the capillary tube 110 is surface activated in an $O_2$ plasma (March Plasma Asher). The activated surface is then treated with 3-mercaptopropyl trimethoxysilane (3-MPS) in anhydryous ethanol in an inert environment, and heated at 80-100° C. for 15-60 minutes. Neutravidin 302 is attached to the 3-MPS modified surface through covalent attachment with N-maleimidobutyrl-oxysuccinimide ester (GMBS) 304. First, GMBS is reacted with the inside surface of the capillary at room temperature for 30 minutes. The capillary is flushed with anhydrous ethanol and then a solution of neutravidin:BSA in PBS is introduced into the tube 110 and allowed to react for >1 hr. The tubes are then flushed with PBS. The neutravidin:BSA ratio controls the final density of the seed DNA, which has an influence on DNA synthesis in the device. Biotinylated DNA oligos seeds 150 are attached to the surface by incubating a solution of the oligo, typically 1 µM concentration in PBS, at room temperature for 45 minutes. The tubes are then rinsed thoroughly with PBS. The biotin group may be on the 3'- or 5'-ends of the oligo or internal to the oligo. If the seed oligo is attached to the surface through a 3'-biotin group, a complementary DNA strand that results in a 3' overhang is hybridized to the seed oligo for DNA synthesis to extend from. Using a hybridized oligo strand can enable recycling of the capillary for multiple DNA synthesis cycles by melting the product DNA off of the capillary surface.

In an alternate embodiment, Cu-activated click chemistry is used to attach the seed DNA molecule to the inside of the capillary tube. First, the inside of the capillary tube is surface activated in an $O_2$ plasma (March Plasma Asher). The activated surface is then treated with (3-aminopropyl) tri-ethoxysilane in a mixture of 2% APTES and 5% water in ethanol. The capillary tube 110 is treated with the APTES solution for 5 minutes, drained and flipped. The tube 110 is then drained again after 10 minutes, flipped again, and incubated for 15 minutes. After treatment the tube is rinsed thoroughly with ethanol and heated at 100° C. for 30 minutes. The NHS-PEG-Azide (MW 388.4) is attached to the amino-silanine 312 on the tube walls 110-I tubes by incubating 500 µM NHS-PEG-Azide in the tube 110 in a humidity chamber for 2 hours. NHS-PEG (MW 1000) 314 can be used as a blocking agent and to control the final density of seed DNA in the device. After treatment, the tube is flushed thoroughly with deionized water. An alkyne modified DNA molecule (3' 5-octadiynyl dU) 150 is attached to the azide-modified surface through a reaction mediated by a solution of 1 mM Tris (3-hydroxypropyltri-azolylmethyl) amine (THPTA), 1 mM copper (II) sulfate, 1 mM ascorbic acid, and 1 µM alkyne-DNA. The reagent mixture is incubated in the tube for 2 hours in a humidity chamber, and then rinsed thoroughly with PBS. For DNA synthesis, a complimentary strand is hybridized to the seed DNA molecule. To attach the hybrid strand, 1 µM of the oligo in TE buffer with 50 mM NaCl is incubated in the tube at room temperature for 30 minutes. The tube is then rinsed thoroughly with TE buffer with 50 mM NaCl.

Random access retrieval may require ~$10^3$ unique DNA seed molecules 150 to be immobilized in the tube 110 in a spatially controlled manner. The tubes can be prepared by adding each unique DNA seed molecule sequentially and using photo-activated chemistries, such as photoactivated click reactions (Orski et al., *JACS* 132, 11024 (2010)), to attach a DNA seed molecule containing a particular index in the desired location. Spatial control is achieved by local illumination to activate the surface at the desired location followed by microfluidic introduction of the specified DNA molecule. The process is repeated until the required number of seed molecules have been immobilized.

The DNA seeds 150 are immobilized within different storage locations with the tubes 110. The storage locations are the volumetric storage regions 172 within the tubes 110 that are accessible based on the pixel resolution of the optical controller 170. These volumetric regions 172 are characterized by the two-dimensional area 174 defined at the outer wall of the tube through which light from a single pixel of the optical controller 170 is projected through the wall of the tube 110 into the volumetric region 172 in which a single or a number of different DNA strands are synthesized. Typically, each strand synthesized within each volumetric region 172 will have the same sequence, encoding the same data. That said, the strands within a given volumetric region 172 will have different DNA seeds, in some embodiments, allowing for multiple readout cycles of the encoded data.

In many embodiments, the different storage locations are distributed along a longitudinal length of the each of the tubes. Moreover, the different locations are further preferably distributed at different circumferential positions along an inner surface of the tube. At the same time, in still other embodiments, the volumetric storage regions could be distributed throughout the tubes' volumes.

Various compositions, methods and kits for polynucleotide synthesis from the immobilized seeds are provided in Magyar I. They include, for example, methodologies for engineering the terminal deoxynucleotidyl transferase (TdT) protein/enzyme to control the addition of nucleotides to a growing nucleotide strand.

One methodology described in Magyar I relies on the metallic control of TdT. This approach focuses on the separation of metal ion binding at different sites. If the binding at one site occurs on a condition that does not allow metal binding to another then the enzymes catalytic mechanism can be controlled such that only a single nucleotide is added at a time.

Magyar I further provides methods for control of conformation. Typically, a conformational change occurs during the catalytic cycle of TdT. Leucine 398 flips up intercalating between the last nucleotide on the 3-prime end of the primer strand and the rest of the strand.

Reversibly blocked entrance tunnels (be it by protein engineering, by an exogenous factor added to the solution, etc.) can enable greater control over single nucleotide incorporation.

In one scenario, a reversibly blocked TdT is used in conjunction with metal ion gating in order to give greater spatial and temporal control over DNA synthesis. In this scenario, metal gating is used to control the addition of an incoming nucleotide; nucleotide binding occurs under conditions separate from nucleotide addition. However, an additional level of control is added, as nucleotide binding can now be controlled as well via the reversibly blocked entrance tunnel. The nucleotide binding to the pocket can be gated, such that a single nucleotide is allowed to enter and bind to the active site, but cannot be incorporated due to metal ion constraints, and the nucleotide is sealed into the active site while excess nucleotide is removed from the surrounding solution. The bound nucleotide can be added by introduction of the catalytically necessary metal (or conditions), and the cycle can continue. In this method, nucleotides can also be excluded from the enzyme's active site if desired, similarly to the gated ratcheting engineering methods described in the Magyar I, such as the azobenzene photo-switching molecular staple. Thus, again the specific control over nucleotide binding can yield an enzyme capable of being used in an array format to synthesize multiple strands of DNA with different sequences at once.

DNA synthesis can be further controlled by modulating temperature, pH, light, or another aspect of its environment. In particular, exogenous control of protein conformation can rely on the use of a photo-activatable change in conformation. This may be done through the addition of protein domains that are responsive to exogenous control, such as the CRY2-CIB1 blue-light responsive domains (or versions thereof), that are used to give exogenous control over protein conformation, for example. Alternatively, a photo-activated staple is provided in the protein backbone. The azobenzene photoswitch, for example, switches from trans to cis in the presence of UV light, and back to trans in the presence of visible light or heat. By stapling two parts of the protein backbone responsible for the change in protein conformation, such that the protein conformation change is directly linked to the change in conformation of the photoactivatable staple, the conformation of the protein is directly controlled by light and/or heat. Thus, the enzyme, after inserting a single base, could be locked in a non-ratcheting conformation while excess nucleoside triphosphates containing deoxyribose (dNTPs) are removed from the microfluidic, until a light signal is used to induce conformation change and force the enzyme through the rest of the catalytic cycle. In this manner, nucleotides can also be excluded from the enzyme's active site if desired. This gives greater spatial and temporal control over the enzyme's activity.

Figure 4A:
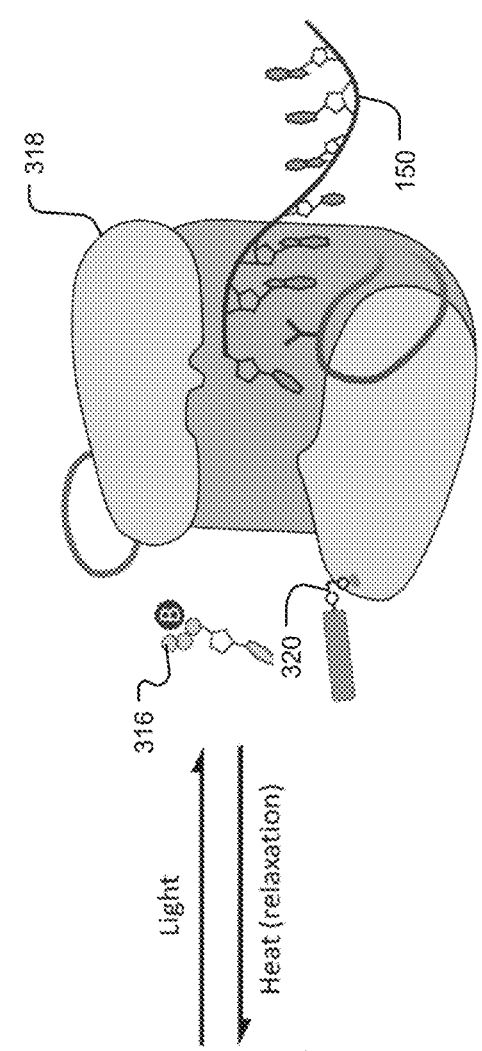
FIGS. 4A and 4B are schematic diagrams providing an overview of an engineered enzyme that enables photo-gated or mediated TDT control.
Figure 4B:
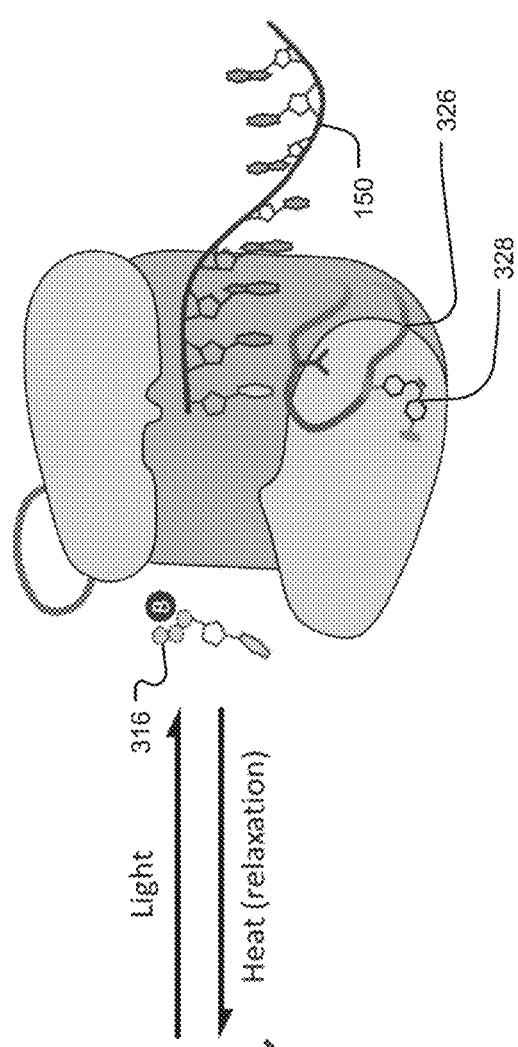

FIGS. 4A and 4B illustrate some enzyme engineering approaches that enable photo-gated or mediated TdT control.

The example of FIG. 4A involves the control of nucleotide entry based on using a "tunnel". In this approach, a photogated molecule 320 is employed to block the tunnel of the TdT molecule 318 and control extension of the DNA strand. The technique relates to the acceptance of an incoming nucleotide and, in one implementation, pertains to designing versions of TdT 318 with a reversibly, or irreversibly, blocked nucleotide entrance tunnel 322, an approach that would help ensure single nucleotide addition.

Irreversibly blocked entrance tunnels 322 for TdT 318 enable a synthesis strategy whereby TdT is initially bound to a nucleotide, then used as a reagent for the attachment of single nucleotides 316 to a growing DNA strand 150, and washed off by denaturing conditions. Thus, the modified TdT enzymes would become single-use, incorporating a single nucleotide before being denatured and removed.

The approach presented in FIG. 4B relies on controlling DNA ratcheting, an approach in which, after TdT 318 performs a nucleotide incorporation, there is a restructuring of a loop 326 in the protein 318, causing the DNA strand 150 to ratchet, thereby enabling a subsequent base addition. This loop 326 can be engineered to be gated by an optically controlled molecular switch 328.

In one example, an engineered enzyme is modified with a photoswitchable molecule. The cross-linking group will change the configuration of the loop responsible for DNA ratcheting. After extension of the DNA by TdT, the protein ratchets the DNA to enable the addition of a subsequent nucleotide. By placing the ratcheting function under photo-control, extension of the DNA can be gated as desired.

Examples of molecular switches for protein control include molecules (e.g., azobenzene, molecules containing azobenzene moieties, other similar structures, etc.) that can induce structural changes in proteins in response to light. As a result, DNA or other polymeric chain synthesis can then be gated through the introduction of such molecules into TdT.

In more detail, an engineered TdT can include one or more amino acid residues of the TdT that are modified, resulting in a TdT capable of controlled addition of nucleotides to the 3' end of a single-stranded polynucleotide. A photoisomerizable engineered TdT, for example, contains one or more amino acid residues of the TdT that are substituted with a non-naturally occurring amino acid comprising a reactive group that can be chemically crosslinked, e.g., to a photoswitchable moiety such as an azobenzene derivative. The azobenzene derivative can regulate/gate entry or binding of a mononucleotide to the active site of TdT.

Other approaches rely on a photoswitchable azobenzene moiety that is modified by the introduction of an attachment site for a click reactive group, e.g., an amine or an alcohol, and introduction of an attachment site for an amino acid side chain. The click reactive group can be selected from a pair of clickable orthogonal groups, the pair comprising: an azide-alkyne groups; tetrazine-norbornene groups; or tetrazine-trans-cyclooctene groups.

Figure 5A:
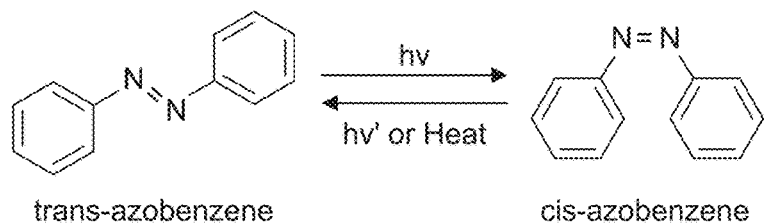
FIGS. 5A, 5B and 5C provide an overview of molecular switches for protein control, with FIG. 5A showing the trans and cis isomers of azobenzene.
Figure 5B:
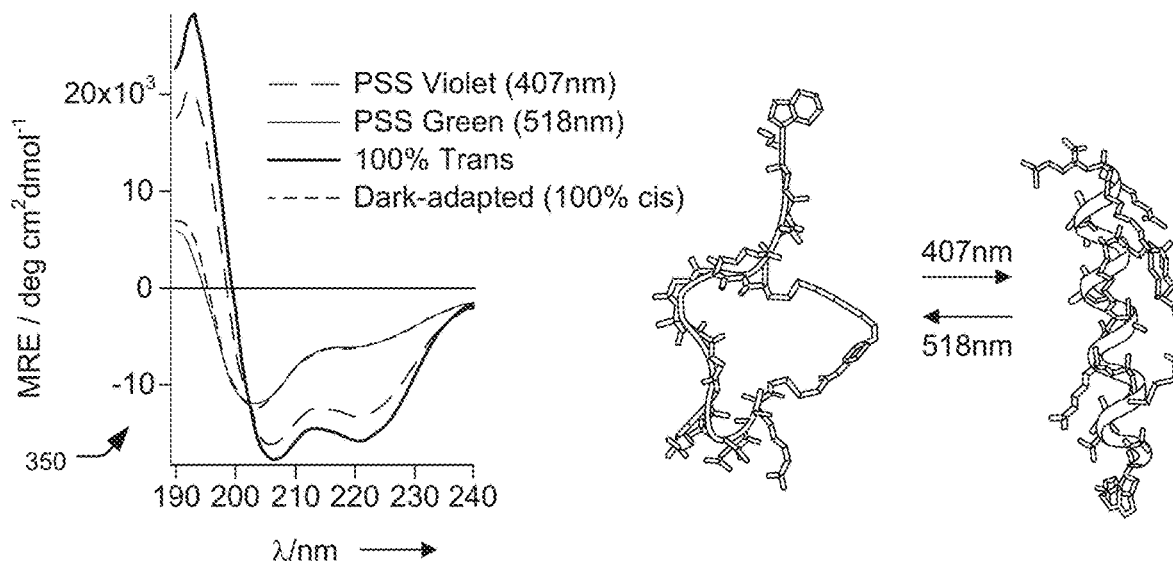
Figure 5C:
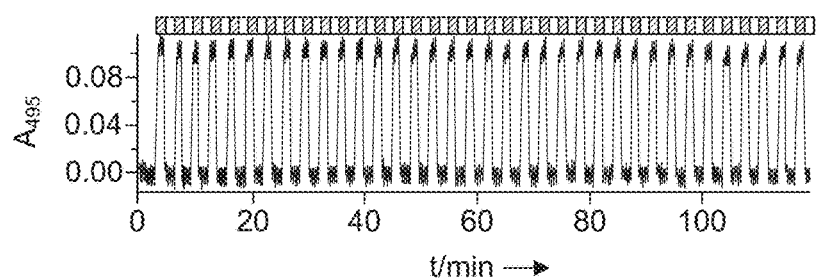

The switch from the trans to the cis isomer occurring in azobenzene exposed to light and heat is shown in FIG. 5A. Photoswitching of helical peptide conformation with bridged azobenzene derivatives is described, for instance, by S. Samanta et al. in Angew. Chem. Int. Ed. 2012, 51, 6452-6455, incorporated herein by this reference in its entirety. As seen in FIG. 5B, when an azobenzene molecule is used to cross-link two portions of a protein, this isomerization can cause structural changes to the peptide. The plot 350 shows the change in the circular dichroism (CD) spectrum that results from the change in ordering of the peptide as a structural change occurs. The absorption of the azobenzene at 495 nm as a function of time presented in FIG. 5C shows relatively regular oscillations from a maximum to a minimum value as it is illuminated with a regularly varying light source that enables the trans-to-cis transition at a second wavelength. Illumination actuates the transformation reducing the absorptivity of the solution containing the azobenzene and increasing the amount of light transmitted. After the illumination is extinguished, the azobenzene will thermally interact with the molecules around it and fall back to the lower energy trans state. This is one test to determine the excitation/relaxation time of the azobenzene, here the relaxation time should be faster than the desired cycle time of nucleotides so that the enzyme will transition to the correct on or off state before errors are made in either adding an unwanted nucleotide or failing to add one at the correct juncture.

Another approach relies on polymerase-nucleotide conjugates as described in Palluk et al., Nature Biotechnology (2018), doi:10.1038/nbt.4173 and International Publication No. WO2017/223517 A1 to D. Arlow et al., both documents being incorporated herein by this reference in their entirety. DNA synthesis is achieved using TdT-dNTP conjugates where a nucleotide is coupled to a TdT enzyme through a cleavable-linker in a site specific manner. The enzyme incorporates the tethered nucleotide onto the 3' end of the DNA strand and prevents further extensions by other TdT-dNTP molecules. In the subsequent step the TdT is cleaved from the nucleotide by light (or a chemical agent), releasing the DNA for further extension. This cycle can be repeated to achieve the desired sequence.

In a further approach, nucleotides with a cleavable moiety attached to the 3'-OH of the nucleotide molecule can be used with TdT or other template independent polymerases to control DNA synthesis, as described in International Publication Nos. WO 2018/102554 A1 to Griswold et al. and WO 2017/156218 A1, to Church et al., both being incorporated herein by this reference in their entirety. This cleavable moiety can be a photolabile group such as a coumarin. The TdT enzyme attaches the modified nucleotide to the 3'-end of the DNA, which terminates extension. In a subsequent step, the 3'-OH can be deprotected using light (or a chemical agent) enabling the addition of subsequent nucleotides. This cycle can be repeated to achieve the desired sequence.

Microfluidic Control of Reagent Introduction

Template independent DNA polymerases, such as terminal deoxynucleotidyl transferase (TdT) are able to catalyze the incorporation of any deoxyribose nucleoside triphosphates (dNTP) (A, C, G, or T) onto 3' end of a seed DNA molecule.

The microfluidic controller 160 enables the synthesis of a defined sequence of nucleotides through the controlled introductions of the reagents required for DNA synthesis into the capillary tube 110 in a sequential fashion (A, C, G, T). This reagent mixture can be an aqueous buffer solution containing the appropriate dNTP, enzyme, metal ion cofactors. The enzyme can either be added together with each nucleotide or through a separate channel. Between synthesis cycles the capillary is flushed with a rinse buffer (i.e. PBS) by microfluidic controller 160 to clear any unreacted nucleotides.

Alternatively, for synthesis with a photo-controlled phosphoramidite chemistry (Konig et al., *Macromol. Rapid Commun.* 38, 1700651 (2017)), the reagent mixture supplied by the microfluidic controller 160 contains phosphoramidite monomers dissolved in anhydrous dichloromethane. Subsequently, the monomer is activated through the introduction of tetrazole in acetonitrile by the microfluidic controller 160. An oxidizing solution is added and incubated and then the capillary is flushed with methanol by the microfluidic controller 160. For photo-deprotection the appropriate region is illuminated by the optical controller 170 and then neutralized using triacetic acid. Coupling, oxidation and photo-deprotection is repeated to obtain the specified sequences.

Figure 6:
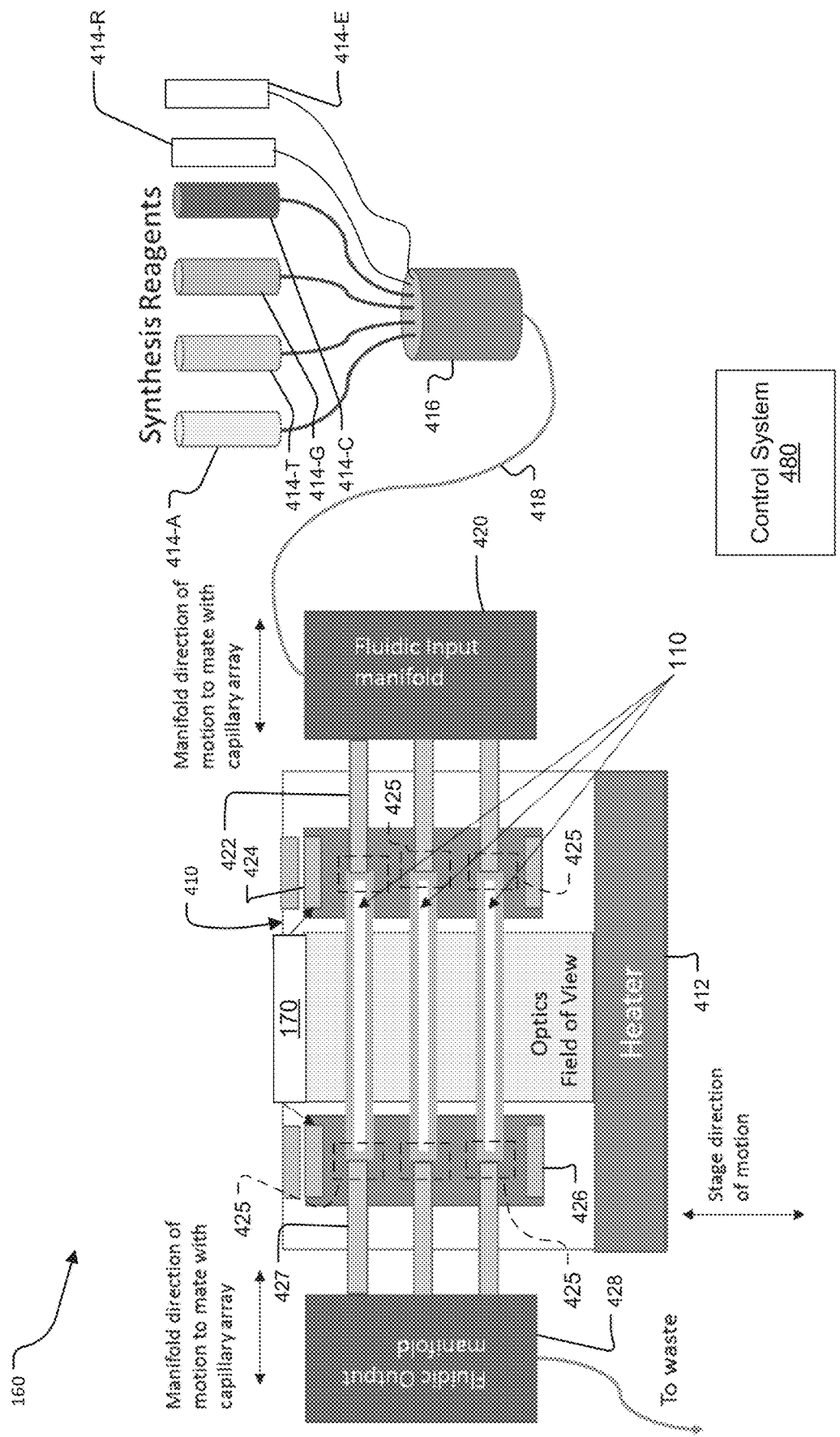
FIG. 6 is a schematic side view of the microfluidic controller with the optical controller under the control of the control system.

FIG. 6 shows an example of a fluidic manifold system 410 of the microfluidic controller 160 that provides the interface with capillary tubes 110 and allows the introduction of reagents for DNA synthesis.

The manifold system 410 provides a means to hold capillary tubes 110 and enable their illumination by the optical controller 170 and thereby modulate synthesis optically. Specifically, the tubes 110 are located in an optical field of view defining the addressable region of the optical controller 170.

Some embodiments include a heater 412 to maintain the optimal temperature for synthesis and to dehybridize the completed product DNA from the surface immobilized seed oligo in the tubes 110. Additionally there are inlets and outlets for reagents. Some embodiments of the manifold incorporate magnets to allow for rapid connection and disconnection of capillary tubes 110.

In more detail, reagent reservoirs contain the required reagents and bases. In the case of DNA synthesis, there is an adenine (A) reservoir 414-A, a cytosine (C) reservoir 414-C, a guanine (G) reservoir 414-G, and a thymine (T) reservoir 414-T to provide the different DNA bases. There is also a rinse reservoir 414-R containing a rinse solution and an elution solution reservoir 414-E containing an elution solution.

A fluid control assembly 416 selectively provides the solutions from each of the reservoirs under the control of a control system 480, which is typically a computer or microcontroller. Typically, the fluid control assembly 416 comprises arrays of electronically controlled pumps and/or electronically controlled valves, under the control of the control system 480 to regulate the flow of the fluids from the reservoirs 414 to the manifold system 410. The control system 480 directs the operation of the functionality of the microfluidic controller 160 and the optical controller 170, by executing software and firmware instructions and/or an operating system. In one example, the control system 480 is a small single-board computer. In other examples, the control system 480 is a microcontroller unit or a system on a chip (SoC), including one or more processor cores along with memory and programmable input/output peripherals such as analog to digital converts and digital to analog converters.

In the illustrated example, the fluid control assembly 416 provides the selected fluids on a single line 418 that terminates in a fluidic input manifold 420. Transfer tubing 422 then carries the fluid from the fluidic input manifold 420 to the various capillary tubes 110.

The capillary tubes are held in a chuck assembly or set of gaskets 424, 426. Here, the chuck assembly includes a set of couplers 425 between the capillary tubes 110 and the respective transfer tubing 422, 427.

A fluidic output manifold 428 receives fluid from the capillary tubes 110 via transfer tubes 427 and provides the fluids to a waste.

Figure 7:
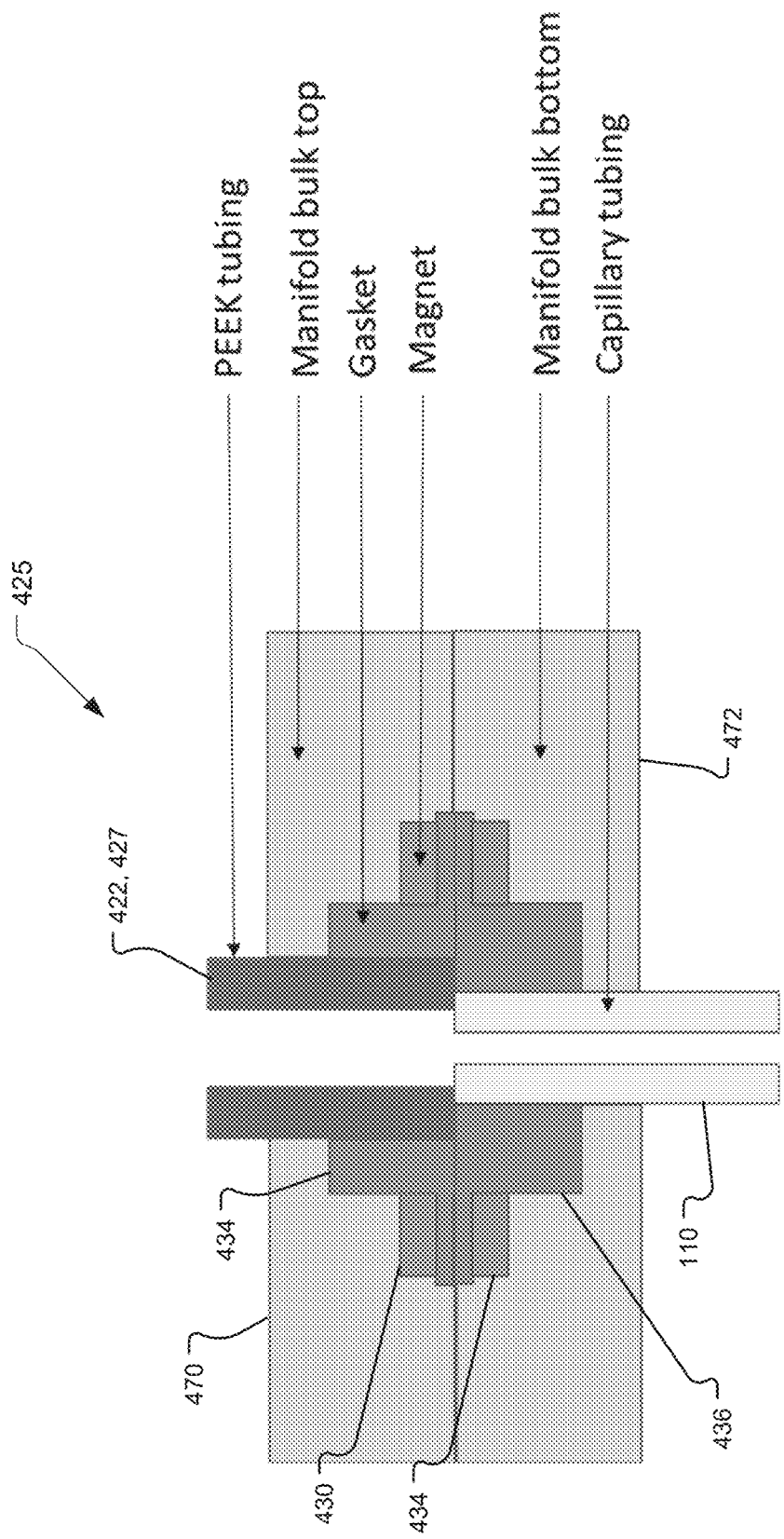
FIG. 7 is a cross-sectional view of a connection of a capillary tube held by a magnetic chuck system.

FIG. 7 shows a cross-sectional view detailing a coupler 425 for each side of each capillary tube 110 shown in FIG. 6. The transfer tubing 422, 427 is held in place by a gasket 434 in one segment or body 470 of each of the couplers and the capillary tube 110 is held in place by a gasket 436 in a second segment or body 472 of the couplers. These two segments 470, 472 house annular magnets 430, 431 to hold the two segments in place and to compress the gaskets 434, 436 against each other. The capillary tubes 110 can be held in the couplers either as an array of individual tubes or a monolithic capillary array.

Figure 8:
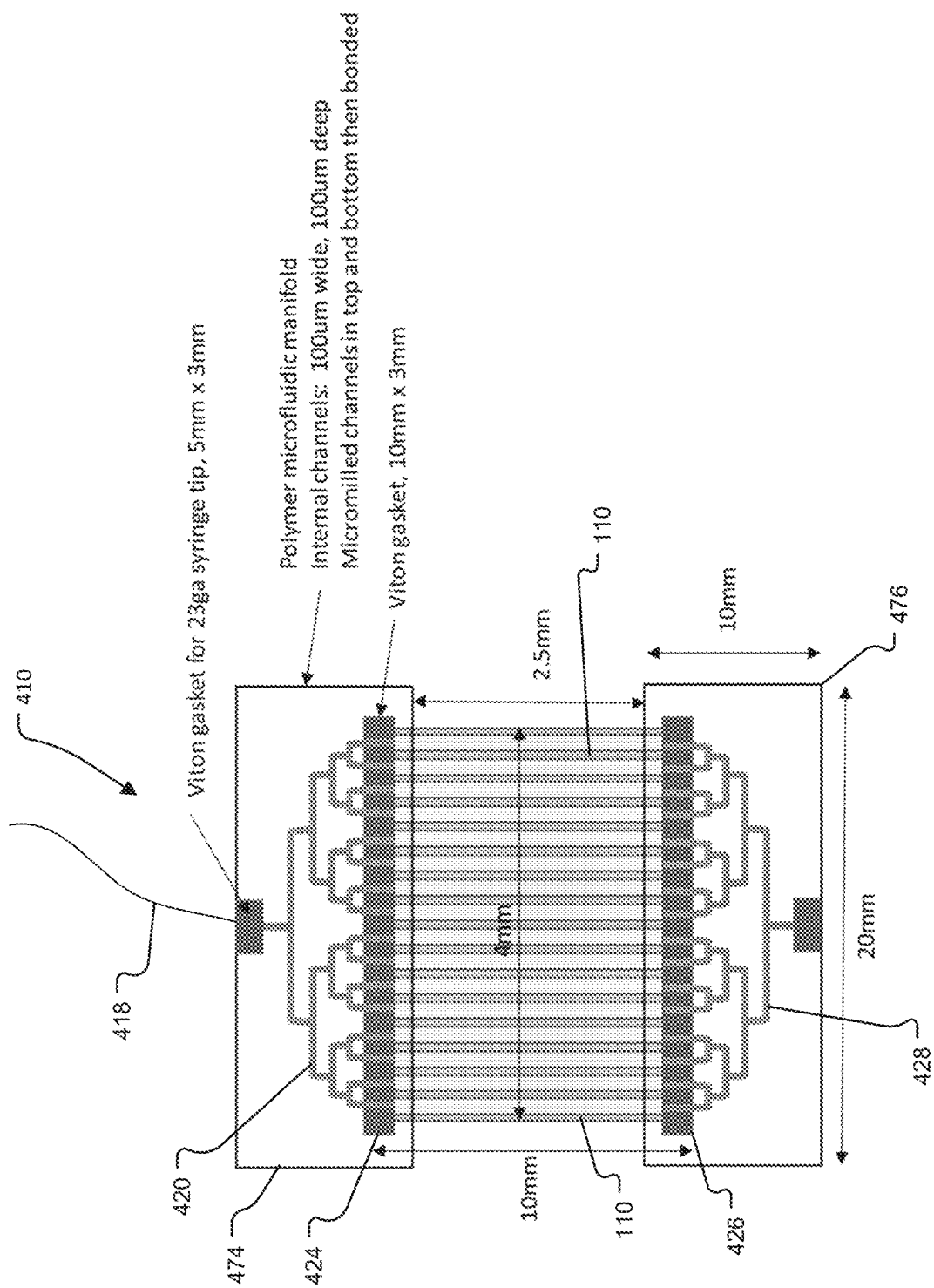
FIG. 8 is a schematic top view of another manifold system of the microfluidic controller.

FIG. 8 shows another manifold system 410. Here, individual capillary tubes 110 are held by the gaskets 424, 426. The gaskets 424, 426 directly connect the respective input manifold 420 and output manifold 428 to a set of capillary tubes 110. The input manifold 420 and output manifold 428 are fabricated in respective polymer blocks 474, 476 in which internal channels (cross-sections of 100×100 micrometers) have been milled to function as the manifold.

Figure 9:
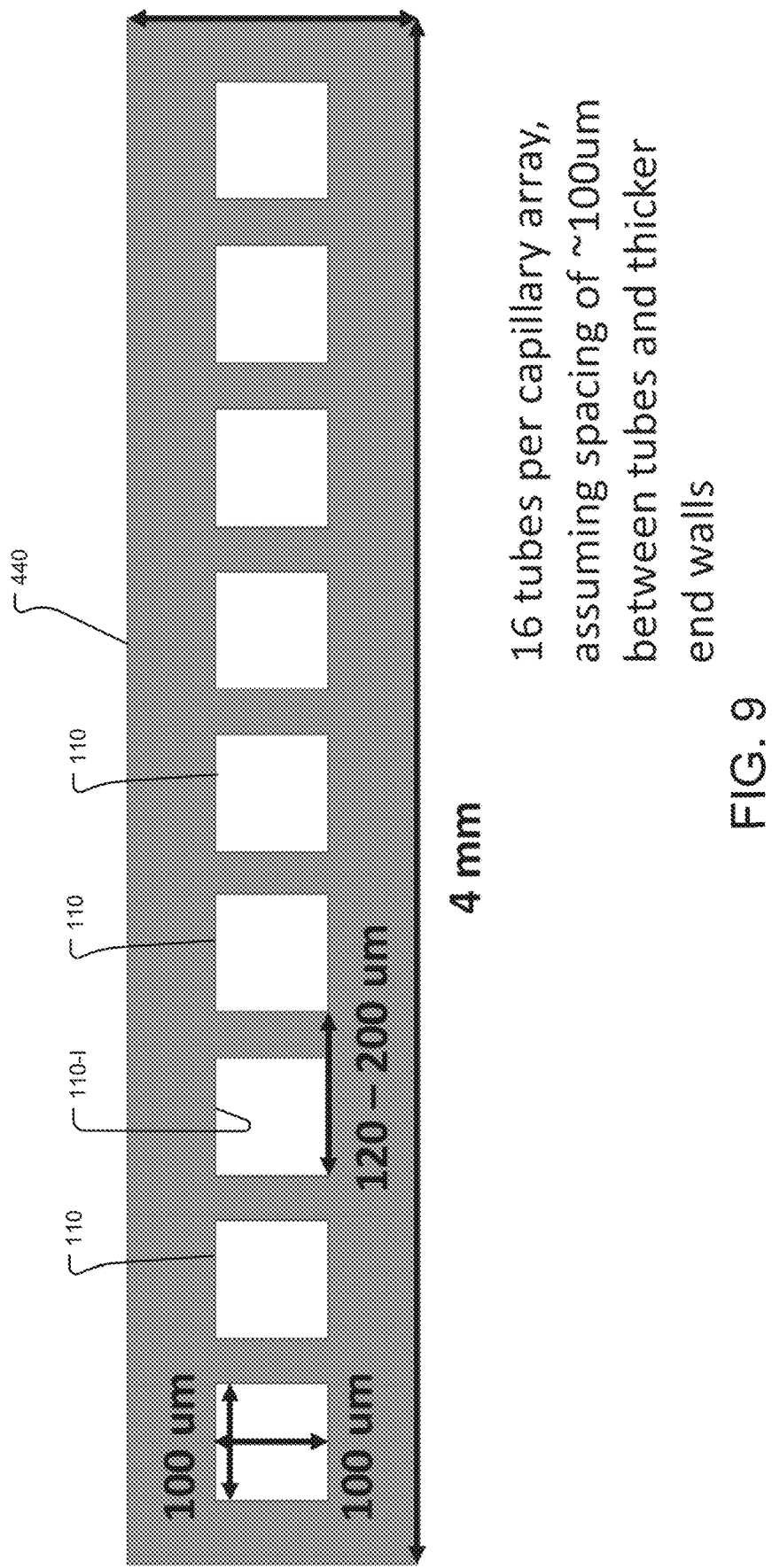
FIG. 9 is a cross-section of a monolithic capillary array that could be used in place of the set of tubes.

FIG. 9 shows a monolithic capillary array that could be used in place of the set of tubes 110 shown in FIG. 8. Here each tube 110 is fabricated in a common glass block 440. The inner walls 110-I of the tubes 110 have a square cross-section of typically less than 1 millimeter (mm) by 1 mm. In the illustrated example, the cross section is about 100 micrometers by 100 micrometers. The pitch between the tubes 110 is possibly between 120 and 200 micrometers, for example.

FIGS. 10A and 10B show another example of a fluidic manifold system 410 of the microfluidic controller 160.

The manifold system 410 includes a heater 412 under a set of capillary tubes 110. The fluidic input manifold 420 and the fluidic output manifold 428 are fabricated in respective blocks 474, 476 that are set into a base frame 450 that clamps the manifolds 420, 428 and the chucks or gaskets 424, 426 around the tubes 110. This compresses the gaskets to create fluidic seals to the capillary tubes 110.

FIG. 11 shows the input manifold 420 fabricated in its block 474 and its internal channels for supplying fluid to a capillary tube 110.

Selection of the desired fluid for introduction into the capillary tubes 110 controlled using a pressure-controlled manifold. The pressure-controlled manifold has individual channels for each nucleotide 460-A, 460-C, 460-G, 460-T, rinse agent 460-R, and elution buffer 460-E. These channels are fabricated in the block 474 of the manifold and feed to common channel 460-B that exits the block 474 to the capillary tube.

Typically, each of the individual channels for each nucleotide 460-A, 460-C, 460-G, 460-T, rinse agent 460-R, and elution buffer 460-E are coupled to the corresponding reservoir 414-A, 414-C, 414-G, 414-T, rinse agent 414-R, and elution buffer 414-E. The fluid control assembly 416 includes a flow device such as a pump and/or valve and/or switch 416-A, 416-C, 416-G, 416-T, 416-R, and 416-E for controlling the flow of the respective fluid. These pumps or valves or switches 416-A, 416-C, 416-G, 416-T, 416-R, and 416-E are under the control of the control system 480.

In an alternative embodiment, the fluidic routing is directly included in the routing element of the manifold. In both embodiments, each channel is individually controlled using a pressure-driven pump or switch or valve.

Figure 12A:
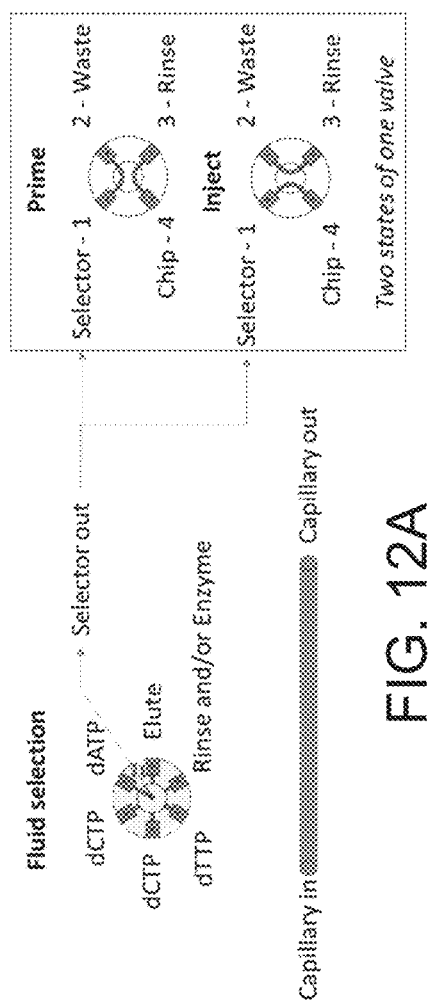
FIGS. 12A and 12B show a rotary selector valve embodiment.
Figure 12B:
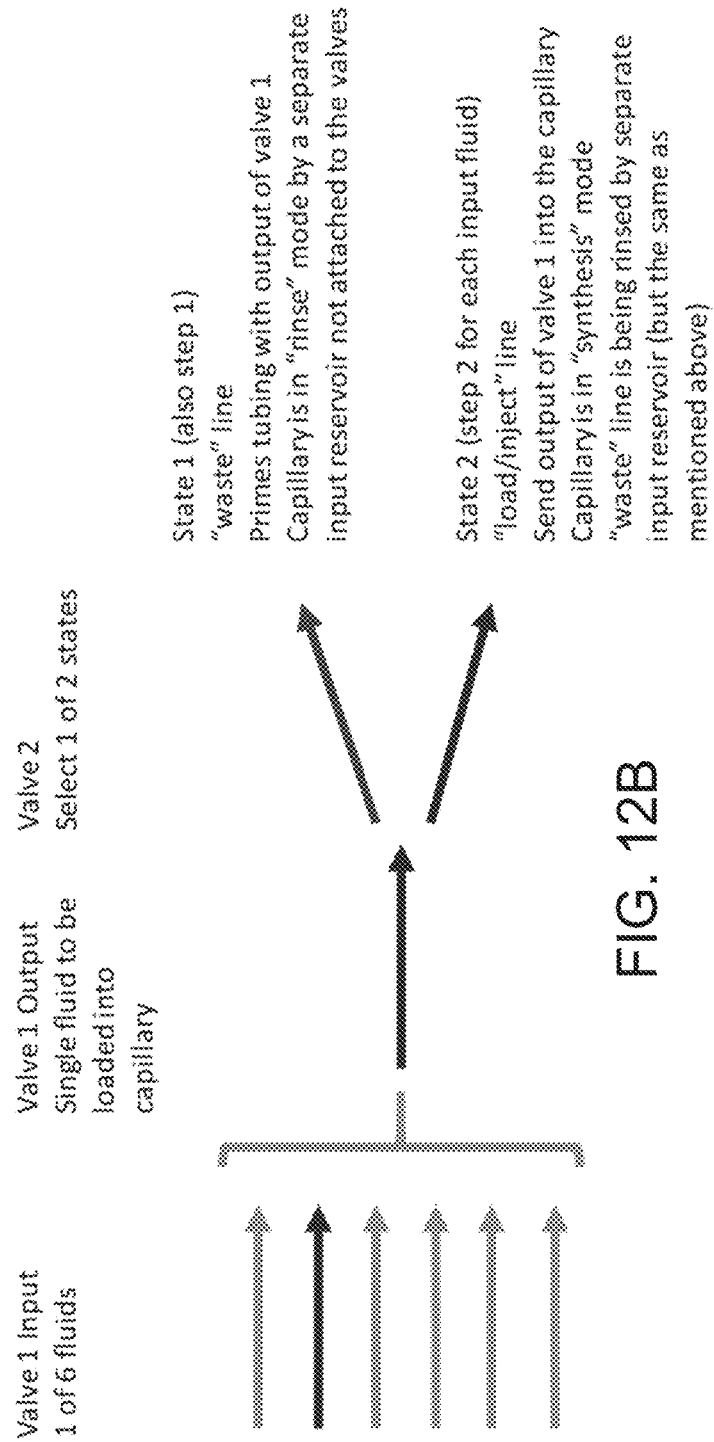

Another embodiment uses electronic rotary selector valves. The valves can either be used to directly switch between each desired input or in a dual state format, where two rotary valves are used in combination for priming and clearance of the tubing and capillaries in a two-step process. One valve is used as the selector choosing the fluid to be directed into the capillaries. The second valve has two states which allow for loading of the output fluid from valve one into the tubing priming the system through the second valve at a higher pressure than can be done through the capillary. During priming, a separate rinse reservoir is pumped through the capillary clearing the prior fluid to minimize crosstalk. Then the capillary state is selected and the output of valve one is pumped into the capillary, as shown in FIGS. 12A and 12B.

The flow rate of each channel is precisely set by using a proportional control loop implemented on the control system 480. The loop is tied in with the switch controls. Unique flow rates are set for each step of the synthesis process. The control loop of the control system 480 is only active when the rotary valves are not switching. A sample step of the valve and flow control for the dual state valve format is as follows:

1. The control system 480 moves the valves or controls the pumps to allow reagent to flow to prime the manifold 420.
2. The control loop of the control system 480 activates to control the flow rate of the reagent during manifold priming.
3. The control loop deactivates.
4. The valves move or the pumps are activated by the control system 480 to allow reagent to flow from the manifold to the capillary 110.
5. The control loop activates to control the flow rate through the capillary 110.
6. The control loop deactivates.

This control sequence together with the manifolds shown enables precise control of the introduction of reagents into a capillary tube 110 by the control system 480 with rapid switching rinsing and switching between reagents.

Figure 13A:
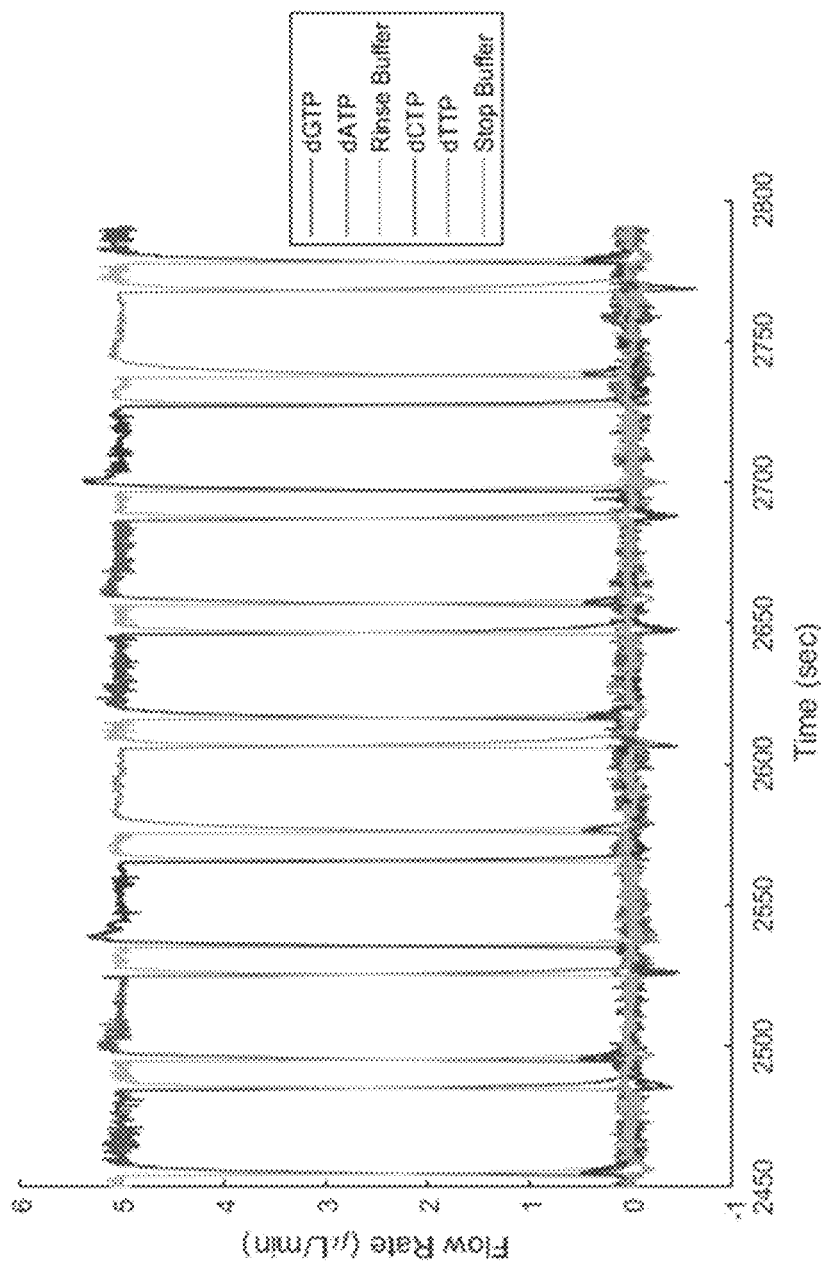
FIG. 13A is a plot of flow rate as a function of time.

The control of reagent introduction into the capillary tube is shown in FIG. 13A, where different nucleotide solutions are introduced sequentially into a capillary tube. Nucleotides were introduced sequentially together with the enzyme terminal deoxynucleotidyl transferase (TdT) and fluid was cycled 30 times between two nucleotides.

Figure 13C:
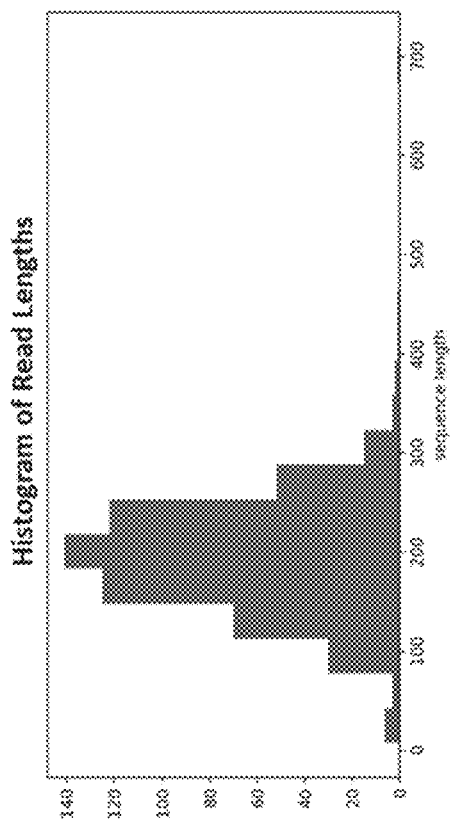
FIG. 13C is a histogram showing the number of observed DNA molecules as function of sequence length.
Figure 13B:
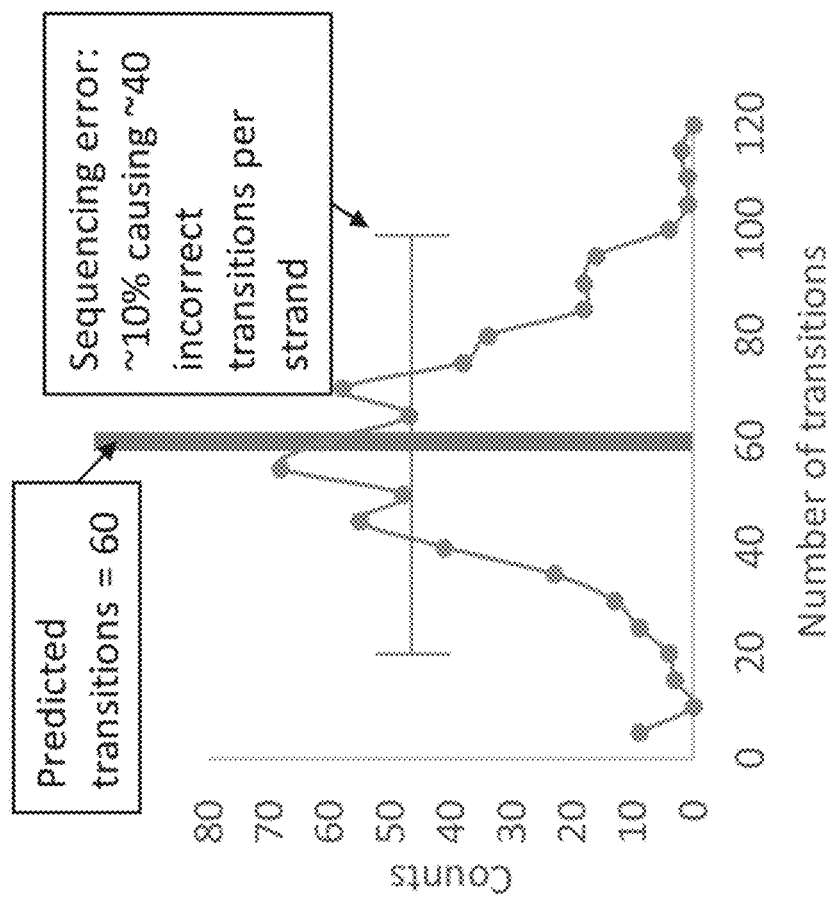
FIG. 13B is a plot of a number of observed DNA sequences (counts) as function of a number of transitions between nucleotides.

FIG. 13B shows DNA sequencing results demonstrating that the synthesized DNA accurately represents the 60 transitions between type of nucleotides, as expected from 30 synthesis cycles. The average length of the synthesized DNA molecules is shown in FIG. 13C.

Optical Multiplexing of Synthesis

DNA synthesis can be controlled using light either using photoprotecting groups as described for phosphoramidite chemistry by Konig et al. or by photocontrol of a template-independent enzyme as described in Magyar I. Nucleotides will be cycled through the capillary device using microfluidics and light will be used to control whether that particular nucleotide is added in a spatially-defined region. Depending on the design of the enzyme and or the chemistry, the light can either be used to initiate or inhibit synthesis. An array of DNA molecules, each with different sequences can be synthesized by actuating the illumination at different physical locations on the surface of the capillary.

Figure 14:
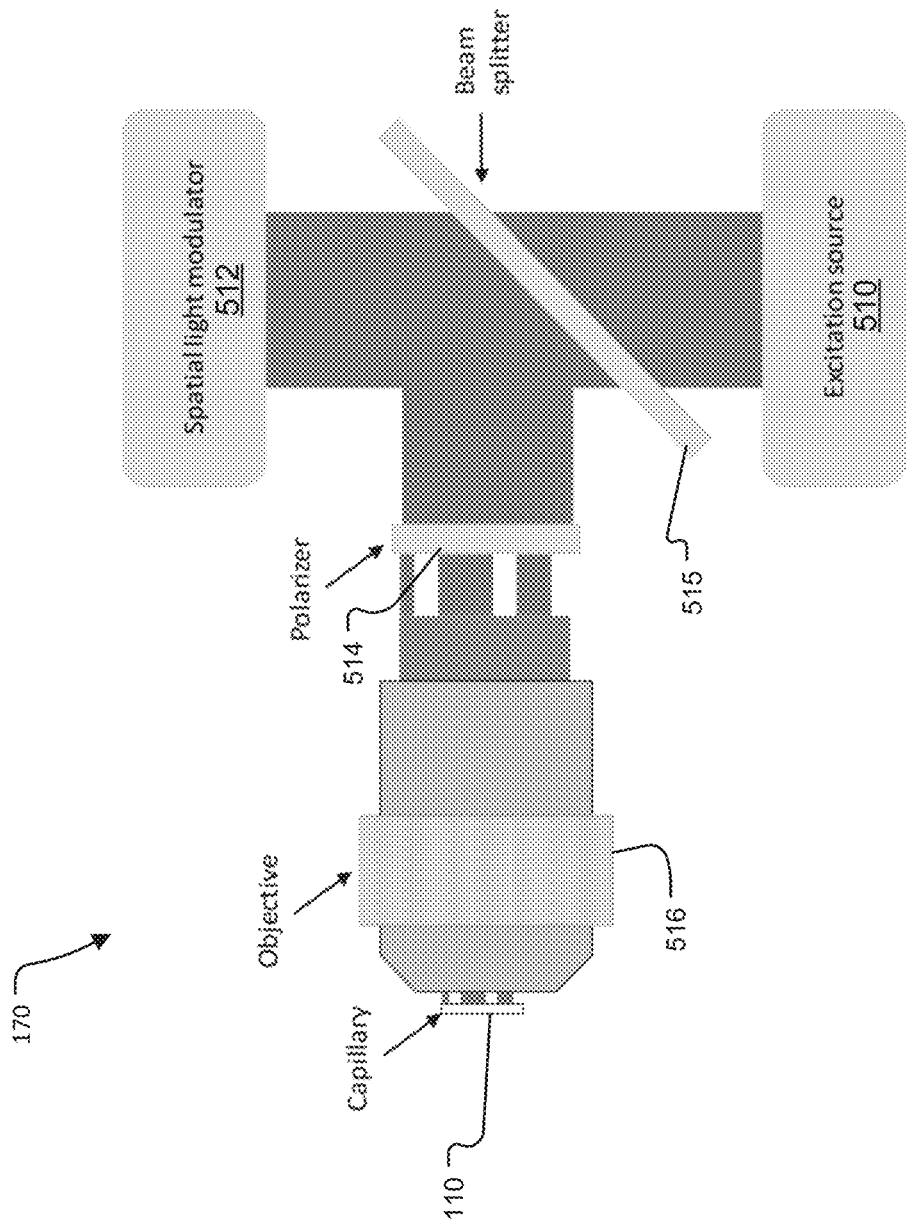
FIG. 14 shows one embodiment of the optical controller.

Some embodiments of this invention can use a spatial light modulator (SLM) in the optical controller 170 to spatially and temporally control illumination, as shown in FIG. 14. This embodiment uses an excitation source 510, such as a lamp or laser operating in the ultraviolet, to illuminate a spatial light modulator 512. A beam splitter 515 directs a light through a polarizer 514. An objective lens system 516 demagnifies the image of the spatial light modulator onto the capillary tube 110.

Figure 15:
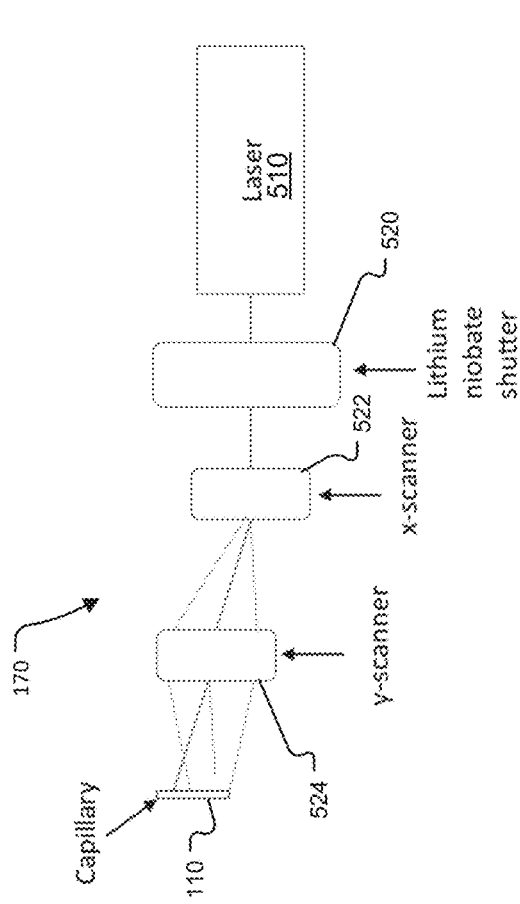
FIG. 15 shows another embodiment of the optical controller.

Alternative embodiments of optical controller 170 use a scanning light source controlled by an acousto-optic modulator together with a rapid beam blanker to spatially and temporally control illumination, as shown in FIG. 15. Here a laser excitation source 510 illuminates lithium niobate shutter device 520. The light is then scanned in an x-axis direction by an x-scanner 522, and in a y-axis direction by a y-scanner 524.

Figure 16:
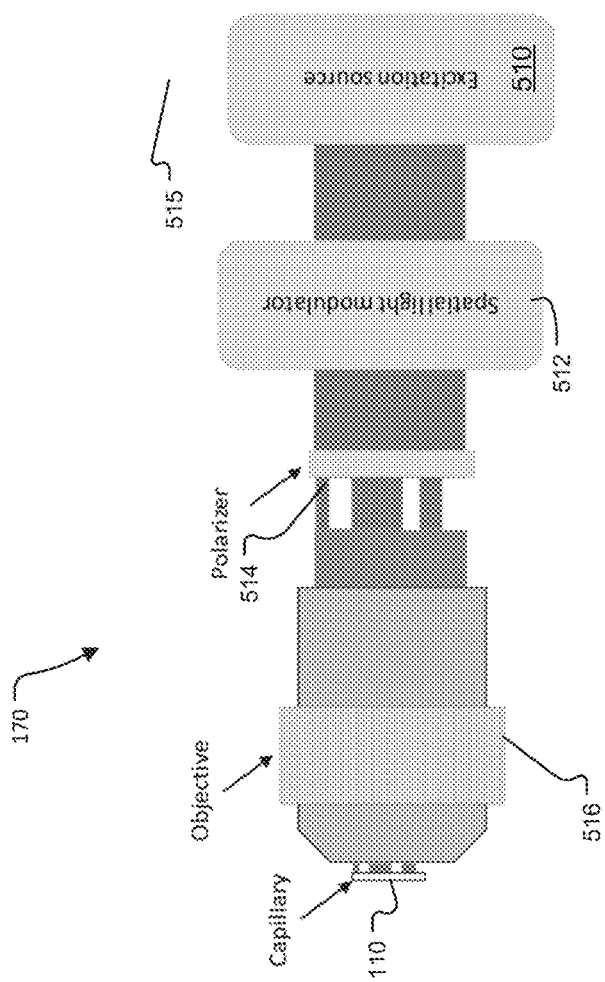
FIG. 16 shows still another embodiment of the optical controller.

In some embodiments the SLM will be a digital micromirror device (DMD) while in other embodiments the SLM will be a reflective phase modulator or polarization rotator based on Liquid Crystal on Silicon (LCoS) technology. Yet more embodiments may utilize a transmissive liquid crystal phase modulator or polarization rotator (FIG. 16).

Figure 17:
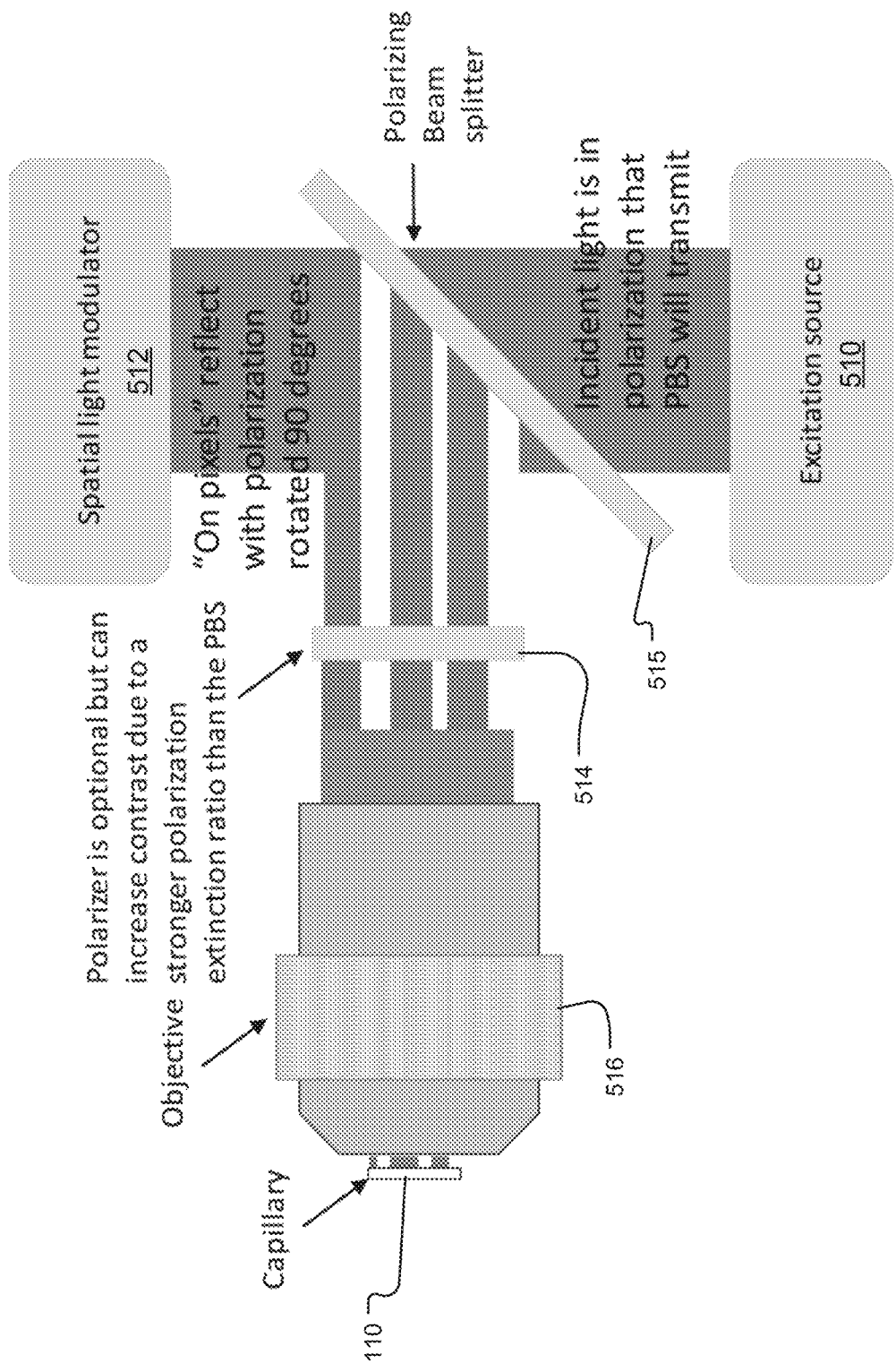
FIG. 17 shows still another embodiment of the optical controller.

Commercially available LCoS devices such as the ThorLabs Exulus-4K1 have a panel resolution of 3840×2160 pixels, providing more than 8 million individually addressable pixels with an active area of 15.6 mm×9.2 mm with a 30 Hz refresh rate. The desired pixel size for photoactuation of DNA synthesis in the capillary is on the order of 1 µm by 1 µm. The SLM can be demagnified with a microscope objective or other combinations of lenses to produce smaller pixels. For example, a demagnification of the Exulus-4K1 by a using 3× microscope objective having a 0.2-0.3 NA can produce pixels that are ~1.3 µm. The LCoS modulates the phase of the light and can be used either in imaging mode or hologram mode to create the intended pattern. A light source incident on the SLM is modulated according to the specified pattern for synthesis and reflected back. A half silvered mirror can be used to direct the light towards the capillary 110. In imaging mode, the phase modulation produced by the SLM can be transformed into amplitude modulation using a polarizer 515 (FIG. 17). This can be combined with a polarizing beam-splitter (instead of a half-silvered mirror) to more efficiently direct the light. In hologram mode the SLM produces the Fourier transform of the intended pattern and then a lens converts angles to positions on the glass capillary. A beam block is used to discard the 0-order diffraction beam. As described above, a microscope objective or combination of lenses is used to demagnify the image and focus it onto the surface of the glass capillary to photoactuate the DNA synthesis.

In the flying-spot scanner a single light source is rastered rapidly over the surface of capillary. A fast beam blank is synchronized with the position of the beam to enable spatially controlled modulation of the light. The flying-spot scanner approach requires a scanning that is fast enough so that the time for the light to sample the synthesis area exceeds the kinetics of the relevant photochemical process. For example, if a photocontrolled enzyme had a switching speed of 1 milliseconds and there are 1 million synthesis pixels the dwell time per pixel must be less than 1 nanosecond. Two acousto-optical scanners combined with a fast beam blanker, such as a lithium niobate shutter can provide rapid scanning of the synthesis area combined with modulation of the light at appropriate positions.

Addressing

To provide addressing of more than $10^6$ sequences per tube 110, each DNA sequence can contain a forward and reverse primer DNA address sequence at the ends of the DNA strand. A 13-nucleotide long DNA strand is sufficient to generate more than 2000 orthogonal forward and reverse primers (Klein et al., Nucleic Acids Research, 44, e43 (2016)). If the synthesis method has a sufficiently low error rate, these addresses can be directly synthesized in the capillary. Alternatively, the address at the 5' end can be pre-introduced into the capillary tube described in the preparation of the capillary tube section. The address on the 3' end can be ligated on to the synthesized strand. If a 3' address is not required a homopolymer can be synthesized on the 3' end to be used for PCR amplification.

For later information retrieval, libraries of forward and reverse primers can be stored in 1536 plates and can be selected using liquid handling robot technology.

DNA Storage

In one embodiment, the DNA-encoded information will be stored in the glass capillary tube 110. After synthesis, a robotic arm will remove the capillary from the synthesis device. The robotic arm may use pneumatics or mechanical actuators to pick up the capillary. The robotic arm will transfer the capillary into a storage pod.

In an alternative embodiment, the DNA can be eluted out of the glass capillary tube and stored in an array. The array could be an industry standard microwell plate, such as a 96-, 384-, or 1536-well plate or could be disposed on a silicon substrate, glass slide, piece of paper or another physical surface or vessel. A robotic arm will be used to move the plate into a storage pod.

Information Retrieval

In one embodiment the glass capillary containing the desired information will be retrieved by the robotic arm and transferred into an instrument for in situ sequencing. The in situ sequencing will use fluorescence-based sequencing by synthesis as described in U.S. Pat. Nos. 9,708,358 and 9,897,791 (and others). In short, a DNA polymerase copies the source DNA strand using fluorescently labeled nucleotides. By monitoring the fluorescence signal at each synthesis step the sequence of the DNA can be determined. In some embodiments, the instrument for in situ sequencing will microfluidically introduce reagents into the capillary, including primers, DNA polymerase, nucleotides, and appropriate buffers. It will have an illumination source to excite the fluorescently labeled nucleotides and a CCD array to capture fluorescence. First, if required, appropriate DNA primers can be robotically retrieved from microplates and introduced into the capillary. The fluorescence sequencing can either be done with all 4 nucleotides in parallel with multi-channel fluorescence detection, or it can be carried out with a single color fluorophore on all 4 nucleotides with the nucleotides fluidically cycled sequentially through the capillary.

In an alternative embodiment, the glass capillary containing the desired information will be retrieved by the robotic arm and transferred into an instrument for in situ polymerase chain reaction (PCR) amplification. The appropriate DNA primers can be robotically retrieved from microplates and introduced into the capillary along with DNA polymerase, nucleotides and buffer for PCR. The targeted DNA information in the capillary will be copied and collected fluidically from the tube. This DNA can then be sequenced in a commercial DNA sequencer such as the Illumina MiSeq, Oxford Nanopore, or Qiagen GeneReader.

In embodiments in which the DNA has already been eluted into an alternative storage array, the appropriate DNA primers can be robotically retrieved from microplates and introduced into the array location containing the desired information along with DNA polymerase, nucleotides and buffer for PCR. The targeted DNA information will be amplified and can be sequenced in a commercial DNA sequencer such as the Illumina MiSeq, Oxford Nanopore, or Qiagen GeneReader.

While this invention has been particularly shown and described with references to preferred embodiments thereof, it will be understood by those skilled in the art that various changes in form and details may be made therein without departing from the scope of the invention encompassed by the appended claims.

What is claimed is:

1. A polymeric chain-synthesizing method, comprising:
providing a manifold system including an input manifold and an output manifold;
forming internal channels in the input manifold and the output manifold;
holding several tubes extending parallel to each other between the input manifold and the output manifold and coupled to the internal channels;
immobilizing seed molecules in the tubes; and
selectively delivering light to different locations of the tubes to mediate or control chemical reactions for synthesis of sequences from the seed molecules to thereby synthesize polymeric chains to encode digital data into the polymeric chains by the selective delivery of the light while the tubes are held between the input manifold and the output manifold; and
introducing different reagents required for synthesis of the polymeric chains by flowing the different reagents through the tubes via the manifold system;
wherein different seed molecules are used to enable random access of the different chains.

2. A method as claimed in claim 1, wherein the polymeric chains include DNA.

3. A method as claimed in claim 1, wherein the seed molecules are immobilized using click chemistry, biotin-streptavidin interactions, or a photo-cleavable or enzymatically-cleavable group.

4. A method as claimed in claim 1, wherein the seed molecules are immobilized using click chemistry, biotin-streptavidin interactions, or a photo-cleavable or enzymatically-cleavable group, where synthesis occurs on a complementary DNA strand that is hybridized to the surface immobilized DNA molecule and leaves a 3' overhang.

5. A method as claimed in claim 1, further comprising sequentially introducing adenine (A), cytosine (C), guanine (G), thymine (T) for synthesis of DNA polymeric chains.

6. A method as claimed in claim 1, further comprising using microfluidics for controlled introductions of the reagents required for synthesis into the tubes.

7. A method as claimed in claim 1, further comprising storing the polymeric chains in the tubes.

8. A method as claimed in claim 1, further comprising sequencing the polymeric chains in the tubes.

9. A method as claimed in claim 1, further comprising eluting the polymeric chains from the tubes and then sequencing the polymeric chains.

10. A method as in claim 9, where the elution is performed by heating the tubes to dehybridize the synthesized chains.

11. A method as claimed in claim 1, further comprising robotically retrieving the tubes from a store to access information encoded in the polymeric chains in the tubes.

12. A method as claimed in claim 1, further comprising in situ sequencing of the chains using sequencing by synthesis, through the sequential microfluidic introduction of fluorescently labeled nucleotides and DNA polymerase and detection of fluorescence.

13. A method as claimed in claim 1, further comprising magnetically securing and fluidically sealing an interface to the tubes.

14. A method as claimed in claim 1, wherein the different locations are distributed along a longitudinal length of the tubes.

15. A method as claimed in claim 1, wherein a spatial light modulator selectively delivers the light to the different locations.

16. A method as claimed in claim 15, wherein the spatial light modulator is a micromirror device.

17. A method as claimed in claim 15, wherein the spatial light modulator is a liquid crystal on a silicon device.

18. A method as claimed in claim 15, wherein the spatial light modulator projects a hologram into the volumetric region.

19. A method as claimed in claim 15, further comprising illuminating the tubes to excite fluorescently labeled nucleotides and capturing fluorescence for in situ sequencing with an image sensor.

20. A polymeric chain-synthesizing method, comprising:
providing a manifold system including an input manifold and an output manifold;
forming internal channels in the input manifold and the output manifold;
holding several tubes extending parallel to each other between the input manifold and the output manifold and coupled to the internal channels;
immobilizing different types of seed molecules in the tubes;
selectively delivering light to different locations of the tubes to mediate or control chemical reactions for synthesis of sequences from the seed molecules to thereby synthesize polymeric chains to encode digital data into the polymeric chains by the selective delivery of the light while the tubes are held between the input manifold and the output manifold;
introducing different reagents required for synthesis of the polymeric chains by flowing the different reagents through internal channels of the input manifold and then into the tubes; and
performing multiple readout cycles using the different types of seed molecules to enable random access of the different chains.

21. A method as claimed in claim 20, further comprising fabricating the input manifold and the output manifold from respective polymer blocks.

22. A method as claimed in claim 20, wherein a pitch between the tubes between 120 and 200 micrometers.

23. A method as claimed in claim 20, further comprising adding and immobilizing the different types of seed molecules sequentially.

24. A method as claimed in claim 23, further comprising attaching the different types of seed molecules at different locations in the tubes.

* * * * *